(12) United States Patent
Baraldi et al.

(10) Patent No.: US 7,435,740 B2
(45) Date of Patent: Oct. 14, 2008

(54) ADENOSINE A$_3$ RECEPTOR MODULATORS

(75) Inventors: Pier Giovanni Baraldi, Ferrara (IT); Pier Andrea Borea, Ferrara (IT); Delia Preti, Ferrara (IT); Mojgan Aghazadeh Tabrizi, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 0 days.

(21) Appl. No.: 11/344,295

(22) Filed: Jan. 31, 2006

(65) Prior Publication Data

US 2006/0178385 A1 Aug. 10, 2006

Related U.S. Application Data

(60) Provisional application No. 60/649,726, filed on Feb. 2, 2005.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ..................... 514/267; 544/251
(58) Field of Classification Search .............. 544/251; 514/267
See application file for complete search history.

(56) References Cited

FOREIGN PATENT DOCUMENTS

SU 213881 3/1968
SU 225203 8/1968

OTHER PUBLICATIONS

Eckstein et al., Synthesis of Optically Active Imidazo[1,2-f]purine Systems, Synthesis, Jul. 1983, 577-579.*
Muller, C., Medicinal Chemistry of Adenosine A3 Receptor Ligands, Current Topics in Medicinal Chemistry, 3, 445-462 (2003).*
Tkachenko, A., et al., Synthesis of Conducting Imidazo[1,2-f]xanthan on Base 8-methyl Mercaptotheofillin, Chemistry of Heterocyclic Compounds, No. 5 (1971).*
Tkachenko et al., "Imidazoles. LIV. Synthesis of imidazo[1,2-f]xanthine derivatives based on 8-amino(alkylamino, arylamino)theophyllines", *Khimiya Geterotsiklicheskikh Soedinenii* 1971, 7(5), 682-685.
Tkachenko et al., "Imidazoles. LV. Synthesis of imidazo[1,2-f]xanthine derivatives based on 8-methyl thiotheophylline", *Khimiya Geterosiklicheskikh Soedinenii* 1971, 7(5), 686-688.
Kochergin et al., "Imidazoles. LIII. Synthesis and pharmacological action of imidazo(1,2-f)xanthene derivatives", *Khimiko-Farmatsevticheskii Zhurnal* 1971, 5(2), 22-26.
Kochergin et al., "Synthesis of condensed imidazole system derivatives from 2-haloimidazoles and 8-haloxanthines," *Khimiya Geterotsiklicheskikh Soedinenii* 1969, (1), 177-178.
Kochergin et al., "Synthesis of imidazo[1,2-f]purine derivatives", *Khimiya Geterotsiklicheskikh Soedinenii* 1965, (3), 475.
Baraldi et al., "A synthetic approach for the preparation of rigid analogs of 1,3-dipropyl-7-methyl-8-aryl/heteroarylstyryl xanthines", *Synthesis* 2001, (5), 773-777.
Tyurin et al., "Computer-aided drug design based on azole-derivative structure-activity relations", *Bashkirskii Khimicheskii Zhurnal* 1997, 4(4), 49-58.
Romanenko et al., "The synthesis and pharmacological activity of the derivatives of 1-methyl-3H-6,9-dihydro-1,2,4-triazino[3,4-f]xanthine", *Khimiko-Farmatsevticheskii Zhurnal* 1986, 20(2), 187-190.
Romanenko et al., "Synthesis and biological properties of substituted triazino[3,4-f]xanthines", *Khimiko-Farmatsevticheskii Zhurnal* 1986, 20(4), 427-430.
Priimenko et al., "Synthesis and study of the reactivity of 1,4-dihydro-1,2,4-triazino(3,4-f)xanthines", *Khimiya i Khimicheskaya Tekhnologiya* 1981, 24(12), 1495-1499.
Beilis et al., "Study of aromatic amines by the method of oxidative voltammetry. VII. Derivatives of 1,2,4-triazine", *Zhurnal Obshchei Khimii* 1979, 49(4), 879-883.
Povstyanoi et al., "Synthesis of 1,4-dihydro-1,2,4-triazino[3,4-f]xanthines", *Khimiya i Khimicheskaya Tekhnologiya* 1975, 18(8), 1316-1319.
Popov et al., "Oxidative condensation of 2-ethylnylbenzimidazole", *Khimiya Geterotsiklicheskikh Soedinenii* 1974, (12), 1696.
Povstyanoi et al., "Synthesis of condensed 1,2,4-triazine systems from 2(8)-methylmercaptoimidazoles", *Khimiya Geterotsiklicheskikh Soedinenii* 1974, (12), 1696-1697.
Povstyanoi et al., "Single-stage synthesis of 1,4-dihydro derivatives of as-triazino(3,4-f)xanthine", *Ukrainskii Khimicheskii Zhurnal* (Russian Edition) 1974, 40(2), 215-216.
Zelnick et al., "Purines. I. Ketones attached through an α-position to a theophylline, 8-bromotheophylline, or theobromine nucleus", *Bulletin de la Societe Chimique de France* 1956, 888-892.
Romanenko et al., "Reaction of 7-(acylmethyl)-8-bromo-8-methylxanthines with formamide", *Khimiya Geterosiklicheskikh Soedinenii*, 1986, (8), 1133-35. CAN 106:176323.

* cited by examiner

*Primary Examiner*—James O. Wilson
*Assistant Examiner*—Erich A Leeser
(74) *Attorney, Agent, or Firm*—Paivi Kukkola

(57) ABSTRACT

A class of novel antagonists for the adenosine A$_3$ receptor are disclosed. These compounds are useful as therapeutic agents for a number of diseases and medical conditions that are mediated by the A$_3$ receptor. The compounds of this invention are also useful as diagnostic agents for the A$_3$ receptor.

18 Claims, No Drawings

ADENOSINE $A_3$ RECEPTOR MODULATORS

This application claims the benefit of U.S. Provisional Application No. 60/649,726, filed Feb. 2, 2005.

BACKGROUND OF THE INVENTION

1. Field of the Invention

This invention pertains to new adenosine $A_3$ receptor antagonists and methods of their use.

2. Description of Related Art

Adenosine exerts a number of physiological functions through activation of four cell membrane receptors classified as $A_1$, $A_{2A}$, $A_{2B}$ and $A_3$. The most recently discovered subtype, the $A_3$ subtype, has been the subject of intensive pharmacological characterization. Although all adenosine subclasses belong to the G protein-coupled receptors they are associated with different second messenger systems. The $A_3$ subtype is believed to have a characteristic second messenger profile, in that it has been shown to mediate adenylyl cyclase inhibition and phospholipase C activation.

The adenosine $A_3$ receptor is also believed to play a role in modulation of cerebral ischemia, inflammation, ischemic heart pre-conditioning and asthma. Thus, $A_3$ receptor agonists find use in the treatment of these diseases. The $A_3$ receptor is also a therapeutic target on cell growth, on apoptosis, on leukemic Jurkat T cells, on the human malignant melanoma A375 cell line and on human neutrophils. The human cloned $A_3$ adenosine receptor was first characterized with $N^6$-(4-amino-3-[125I]iodobenzyl)adenosine.

SUMMARY OF THE INVENTION

The compounds of this invention are potent and selective $A_3$ adenosine receptor modulators, e.g., adenosine receptor antagonists. Compounds of the invention include, inter alia, 1-aralkyl-3-alkyl-1H,6H-pyrrolo[2,1-f]purine-2,4-diones, 1-aralkyl-3-alkyl-1H,8H-imidazo[2,1-f]purine-2,4-diones, and 8-aralkyl-6-alkyl-1,4-dihydro-8H-1,2,4a,6,8,9-hexaazafluorene-5,7-diones.

In one embodiment, compounds of this invention can be described by the general Formula (I):

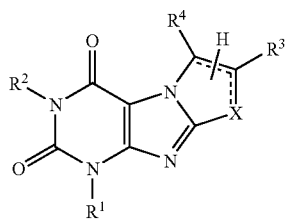

(I)

wherein

X is CH or N;

$R^1$ and $R^1$ are each independently hydrogen, alkyl, substituted alkyl, aralkyl, substituted aralkyl, alkenyl, substituted alkenyl, alkynyl, substituted alkynyl, aryl, or substituted aryl;

$R^3$ is aryl, substituted aryl, alkyl, substituted alkyl, aralkyl, substituted aralkyl;

$R^4$ is hydrogen, alkyl, substituted alkyl, aralkyl, substituted aralkyl, aryl, or substituted aryl; and one of the dashed lines represents a double bond and the other represents a single bond;

or a pharmaceutically acceptable salt thereof.

In another aspect, this invention provides compounds of the following Formula (II):

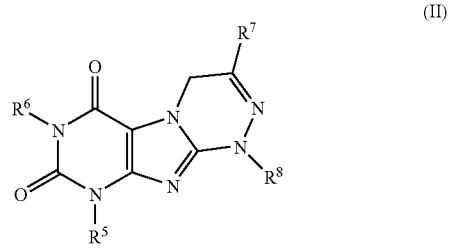

(II)

wherein $R^5$ and $R^6$ are each independently hydrogen, alkyl, substituted alkyl, aralkyl, substituted aralkyl, alkenyl, substituted alkenyl, alkynyl, substituted alkynyl, aryl, or substituted aryl;

$R^7$ is alkyl, substituted alkyl, aryl, substituted aryl, aralkyl, or substituted aralkyl; and $R^8$ is alkyl, substituted alkyl, aralkyl, substituted aralkyl, aryl, or substituted aryl;

or a pharmaceutically acceptable salt thereof.

The compounds of this invention, including both Formula (I) and (II), are useful in the treatment of cerebral ischemia, inflammation, neurodegeneration, glaucoma, ischemic heart pre-conditioning, cancer and asthma in mammals. The compounds of this invention are also useful as tools for the investigation of therapeutic targets on cell growth, on apoptosis, on leukemic Jurkat T cells, on human malignant melanoma A375 cell line and on human neutrophils. These compounds can also be used in screening assays to assess the activity of compounds in modulating the $A_3$ receptor.

DETAILED DESCRIPTION OF THE INVENTION

Chemical and Pharmaceutical Compositions.

The compounds of this invention can be described by the general Formula (I):

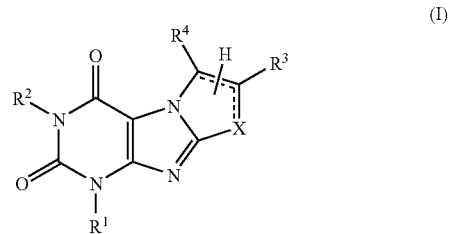

(I)

wherein

X is CH or N;

$R^1$ and $R^2$ are each independently hydrogen, alkyl, substituted alkyl, aralkyl, substituted aralkyl, alkenyl, substituted alkenyl, alkynyl, substituted alkynyl, aryl, or substituted aryl;

$R^3$ is aryl, substituted aryl, alkyl, substituted alkyl, aralkyl, substituted aralkyl;

$R^4$ is hydrogen, alkyl, substituted alkyl, aralkyl, substituted aralkyl, aryl, or substituted aryl;

or a pharmaceutically acceptable salt thereof.

In preferred embodiments, $R^4$ is hydrogen, alkyl or substituted alkyl, more preferably $R^4$ is hydrogen. In preferred embodiments, $R^3$ is alkyl, more preferably methyl, substituted alkyl, aryl, more preferably phenyl, substituted aryl, preferably substituted phenyl, more preferably 4-substituted phenyl, still more preferably 4-fluorophenyl, or aralkyl. In preferred embodiments, $R^1$ and $R^2$ are each independently hydrogen, alkyl, substituted alkyl, or aralkyl. More preferably, $R^2$ is alkyl, still more preferably propyl.

Thus, in certain embodiments, the invention provides a compound represented by Formula (Ia):

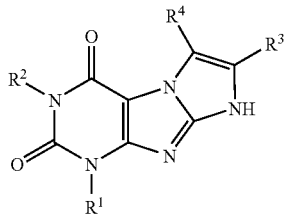

(Ia)

wherein $R^1$, $R^2$, $R^3$ and $R^4$ are as described above; or a pharmaceutically acceptable salt thereof.

In preferred embodiments of Formula (Ia), $R^4$ is hydrogen, alkyl or substituted alkyl, more preferably $R^4$ is hydrogen. In preferred embodiments, $R^3$ is alkyl, more preferably methyl, substituted alkyl, aryl, more preferably phenyl, substituted aryl, preferably substituted phenyl, more preferably 4-substituted phenyl, still more preferably 4-fluorophenyl, or aralkyl. In preferred embodiments, $R^1$ and $R^2$ are each independently hydrogen, alkyl, substituted alkyl, or aralkyl. More preferably $R^2$ is alkyl, still more preferably propyl, and $R^1$ is aralkyl, more preferably benzyl.

In certain embodiments, the invention provides a compound represented by Formula (Ib):

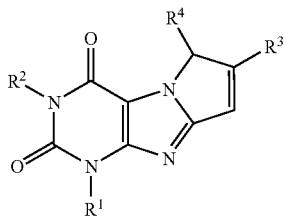

(Ib)

wherein $R^1$, $R^2$, $R^3$ and $R^4$ are as described above; or a pharmaceutically acceptable salt thereof.

In preferred embodiments of Formula (Ib), $R^4$ is hydrogen, alkyl or substituted alkyl. In preferred embodiments, $R^3$ is alkyl, substituted alkyl, aryl, more preferably phenyl, substituted aryl, preferably substituted phenyl, more preferably 4-substituted phenyl, still more preferably 4-fluorophenyl, or aralkyl. In preferred embodiments, $R^1$ and $R^2$ are each independently hydrogen, alkyl, substituted alkyl, or aralkyl. More preferably, $R^1$ is alkyl, still more preferably propyl, and $R^2$ is aralkyl, more preferably benzyl.

Another aspect of this invention provides compounds of Formula (II):

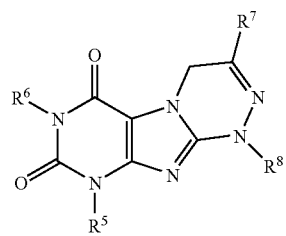

(II)

wherein $R^5$ and $R^6$ are each independently hydrogen, alkyl, substituted alkyl, aralkyl, substituted aralkyl, alkenyl, substituted alkenyl, alkynyl, substituted alkynyl, aryl, or substituted aryl;

$R^7$ is alkyl, substituted alkyl, aryl, substituted aryl, aralkyl, or substituted aralkyl; and $R^8$ is alkyl, substituted alkyl, aralkyl, substituted aralkyl, aryl, or substituted aryl;

or a pharmaceutically acceptable salt thereof.

It will be appreciated by one of ordinary skill in the art that the compounds of the invention may in certain instances exist in tautomeric forms (e.g., a form in which a double bond is transposed from the structure shown herein). Such tautomeric forms are within the scope of this invention.

As used herein, the term "alkyl" refers to monovalent straight, branched or cyclic paraffinic hydrocarbon groups that may be derived from an alkane by dropping one hydrogen from the formula. Alkyl groups preferably have from 1 to 20 carbon atoms (3 to 20 carbon atoms for cycloalkyls), more preferably 1 to 10 carbon atoms ("lower alkyl") (3 to 10 carbon atoms for lower cycloalkyls) and most preferably 1 to 6 carbon atoms (3 to 6 carbon atoms for cycloalkyls). This term is exemplified by groups such as methyl, ethyl, npropyl, iso-propyl, n-butyl, iso-butyl, n-hexyl, and the like. The terms "alkylene" and "lower alkylene" refer to divalent radicals of the corresponding alkane.

Further, as used herein, other moieties having names derived from alkanes, such as alkoxy, alkanoyl, alkenyl, cycloalkenyl, etc., when modified by "lower," have carbon chains of ten or fewer carbon atoms. In those cases where the minimum number of carbons required are greater than one, e.g., alkenyl and alkynyl (minimum of two carbons) and cycloalkyl (minimum of three carbon atoms), it is to be understood that the term "lower" means at least the minimum number of carbon atoms.

As used herein, the term "substituted alkyl" refers to an alkyl group, having from 1 to 5 substituents, and preferably 1 to 3 substituents. Preferred substituents include phenyl, alkoxy, substituted alkoxy, cycloalkoxy, substituted cycloalkoxy, cycloalkyl, substituted cycloalkyl, cycloalkenyl, substituted cycloalkenyl, alkynyl, acyl, acylamino, acyloxy, amino, aralkyl, substituted aralkyl, aryl, substituted aryl, carboxyl, carboxyalkyl, cyano, halogen, hydroxyl, aryloxy, substituted aryloxy, heteroaryl, heteroaryloxy, heterocyclyl, hydroxylamino, alkoxyamino, nitro, alkylthio, substituted alkylthio, arylthio, substituted arylthio, and mono- and di-alkylamino, mono- and di-(substituted alkyl)amino, mono- and di-arylamino, mono- and diheteroarylamino, and unsymmetric di-substituted amines having different substituents selected from alkyl, aryl, aralkyl, and heteroaryl. As used herein, other moieties having the prefix "substituted" are intended to include one or more of the substituents listed above.

As used herein, the term "alkoxy" refers to the group "alkyl-O-", where alkyl is as defined above. Preferred alkoxy groups include methoxy, ethoxy, n-propoxy, isopropoxy, n-butoxy, tert-butoxy, sec-butoxy, n-pentoxy, n-hexoxy, 1,2-dimethylbutoxy, and the like.

As used herein, the term "alkenyl" refers to unsaturated aliphatic hydrocarbon groups having one or more double bonds, preferably having from 2 to 10 carbon atoms, and more preferably 2 to 6 carbon atoms. This term is exemplified by such groups as ethenyl, n-propenyl, iso-propenyl, and the like.

As used herein, the term "alkynyl" refers to alkynyl groups preferably having from 2 to 10 carbon atoms and more preferably 2 to 6 carbon atoms and having at least 1 and preferably from 1-2 sites of alkynyl unsaturation.

As used herein, the term "aryl" refers to aromatic moieties having from 5 to 14 atoms in the aromatic ring system. An aryl group can be carbocyclic (e.g., phenyl, naphthyl) or heterocyclic (a heteroaryl group) having from 1 to 6 heteroatoms (selected from N, S, and O) in the aromatic ring system. Exemplary aryl groups include phenyl, naphthyl, pyridyl, pyrazinyl, thiophenyl, benzothiophenyl, furanyl, benzofuranyl, quinolyl, quinazolyl, indolyl, thiazolyl, oxazolyl, and tetrazolyl. A preferred aryl group is a phenyl group.

Aryl groups can be substituted with from 1 to 10 substituents (depending on the number of atoms in the aromatic ring(s)) selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, alkaryl, aryl, aryloxy, azido, carboxyl, carboxylalkyl, cyano, halo, nitro, heteroaryl, heteroaryloxy, and trihalomethyl. Preferred substituents include alkyl, alkoxy, halo, cyano, and trihalomethyl. Phenyl groups can optionally be substituted with from 1 to 5 substituents and preferably 1 to 3 substituents.

As used herein, the term "aralkyl" refers to an alkyl group (preferably a lower alkyl group) substituted with an aryl group as defined herein. A "substituted aralkyl" group is an aralkyl in which one or more hydrogen atoms in either the alkyl or the aryl portion of the aralkyl moiety has (have) been substituted by one of the substituents described above for alkyls and aryls, respectively. Preferred aralkyl groups include benzyl, 4-fluorobenzyl, 2-pyridinylmethyl, phenethyl, and the like.

As used herein, the terms "halo" or "halogen" refer to fluoro, chloro, bromo and iodo and preferably is either fluoro or chloro.

The compounds of the invention can be named according to several naming conventions, e.g., as purine or xanthine derivatives or as azaindene derivatives. For example, compound 1 herein can be named as "1-Benzyl-7-phenyl-3-propyl-1H,6H-pyrrolo[2,1-f]purine-2,4-dione", "-Benzyl-7-phenyl-3-propyl-1H-pyrrolo[1,2-f]purine-2,4(3H,6H)-dione" or as "7-Benzyl-2-phenyl-5-propyl-1H,7H-3a,5,7,8-tetraaza-cyclopenta[a]indene4,6-dione"; these names are equivalent. One of ordinary skill in the art will be able to determine the corresponding structure for any compound named herein.

"Pharmaceutically acceptable salts" refers to salts of a compound, which can be derived from a variety of organic and inorganic counter ions well known in the art and include, by way of example, sodium, potassium, calcium, magnesium, ammonium, tetraalkylammonium, and the like. When the molecule contains a basic functionality, salts of organic or inorganic acids, such as hydrochloride, hydrobromide, tartrate, mesylate, acetate, maleate, oxalate, and the like, can be used as the pharmaceutically acceptable salt. This invention also encompasses pharmaceutical compositions that are known to those of skill in the art, in which the compounds of this invention, or their pharmaceutically acceptable salts, are used as the active ingredient.

As used herein, an "modulator" is any ligand that binds to receptors and thereby alters the proportion of them that are in an active form, resulting in a biological response. An "antagonist" is a ligand that binds to or otherwise blocks a receptor and prevents activation of the receptor.

This invention also encompasses compounds of Formula (I) and Formula (II) which are labeled with radioactive isotopes, such as, but not limited to tritium ($^3H$), carbon ($^{14}C$), iodine ($^{125}I$), phosphorus ($^{31}P$, $^{32}P$, $^{33}P$), and sulfur ($^{35}S$). The compounds may also be labeled in other ways, e.g., fluorescently or with PET (Positron Emission Tomography) or SPECT (Single Photon Emission Tomography) labels.

For example, the 3-position of Formula (I) or the 4-position of Formula (II) may be labeled with tritium. As another example, the groups at the $R^1$ or $R^2$ or $R^3$ positions of Formula (I), or at the $R^4$ or $R^5$ or $R^7$ positions of Formula (II), may also be labeled with radioactive isotopes such as tritium or carbon isotopes (e.g., $^3H$ or $^{14}C$).

Also known is the use of stable isotopes, such as deuterium ($^2H$) and $^{13}C$ that are detected by magnetic resonance imaging or mass spectrometry. The compounds of this invention may also be labeled or derivatized, for example, for kinetic binding experiments, for further elucidating metabolic pathways and enzymatic mechanisms, or for characterization by methods known in the art of analytical chemistry.

As used herein, the term "labeled" includes the use of any of the isotopically substituted forms herein described.

As used herein, the term "therapeutically effective amount" is an amount of an active compound at which a desired pharmacological effect is obtained when administered to a patient.

For therapeutic applications, the compounds of the invention may be suitably administered to a subject such as a mammal (including a cat dog, monkey, horse, cow, sheep, or (most preferably) a human, alone or as part of a pharmaceutical composition, comprising the compound together with one or more acceptable carriers or excipients and optionally other active or inactive ingredients. The carrier(s) must be "acceptable" in the sense of being compatible with the other ingredients of the formulation and not deleterious to the recipient thereof.

Pharmaceutical Compositions

In another aspect, the invention provides pharmaceutical compositions comprising a compound or compounds of the invention, e.g., compounds of Formula (I) or Formula (II).

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the invention is administered transdermally (e.g., using a transdermal patch or iontophoretic techniques). Such formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients are known in the art and described in several issued U.S. patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

In certain preferred embodiments, a compound of the invention is provided in an orally-administered extended-release dosage form. In certain preferred embodiments, the compound is capable of crossing the blood-brain barrier in therapeutically-effective amounts, i.e., the compound can readily penetrate into the central nervous system.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

The present invention further relates to pharmaceutical compositions as described above for use as a medicament.

The present invention further relates to use of pharmaceutical compositions as described herein above for the preparation of a medicament for the treatment of condition that is mediated by the $A_3$ receptor, preferably, cancer, cerebral ischemia, inflammation, ischemic heart pre-conditioning and asthma.

Thus, the present invention also relates to a compound of Formula (I) or Formula (II) for use as a medicament; to the use of a compound of Formula (I) or Formula (II) for the preparation of a pharmaceutical composition for the treatment of condition that is mediated by the $A_3$ receptor, and to a pharmaceutical composition for use in conditions that is mediated by the $A_3$ receptor, comprising a compound of Formula (I) or Formula (II), or a pharmaceutically acceptable salt thereof, in association with a pharmaceutically acceptable diluent or carrier therefore.

Methods of Making the Compounds of the Invention

In another aspect, the invention provides methods for making compounds of the invention, e.g., compounds of Formula (I) or Formula (II). The compounds of the invention can be made by a variety of methods, some of which are described herein. For example, certain 5,6-diamino-1H-pyrimidine-2,4-diones can be prepared as outlined in Scheme 1, and may then be used as precursors for the synthesis of certain compounds of the present invention as exemplified by Schemes 2, 3 and 4.

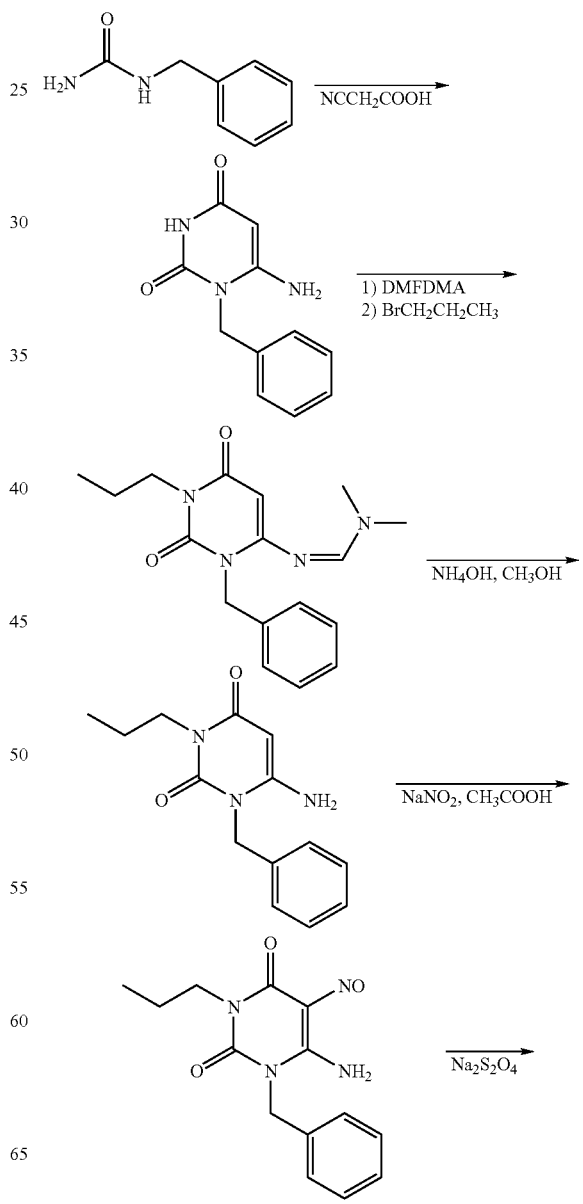

-continued

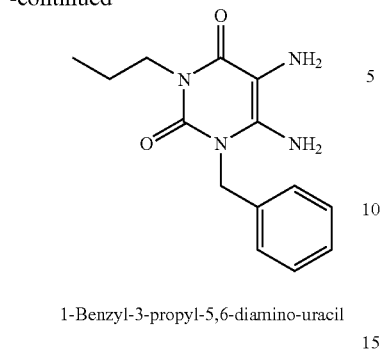

1-Benzyl-3-propyl-5,6-diamino-uracil

As described in more detail in the Examples herein, this synthesis begins with preparation of a 1-substituted 6-amino-uracil (Scheme 1), which, after protection of the 6-amino group, is N-alkylated and deprotected. Treatment with sodium nitrite followed by reduction provides the 5,6-di-amino-uracil, which can then be used in further synthetic steps to obtain compounds of Formula (I) and Formula (II) (Schemes 2, 3 and 4).

Scheme 2

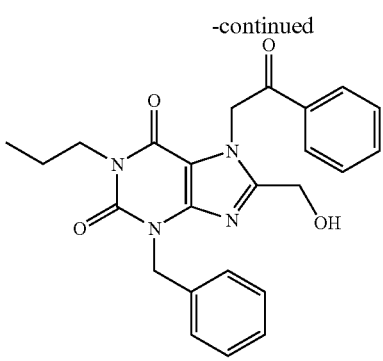

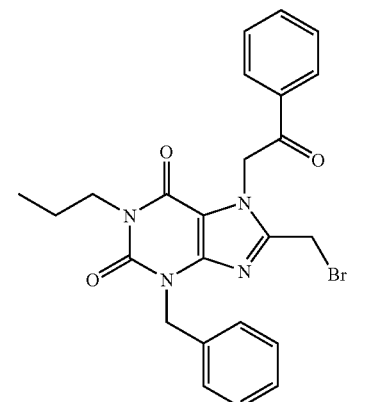

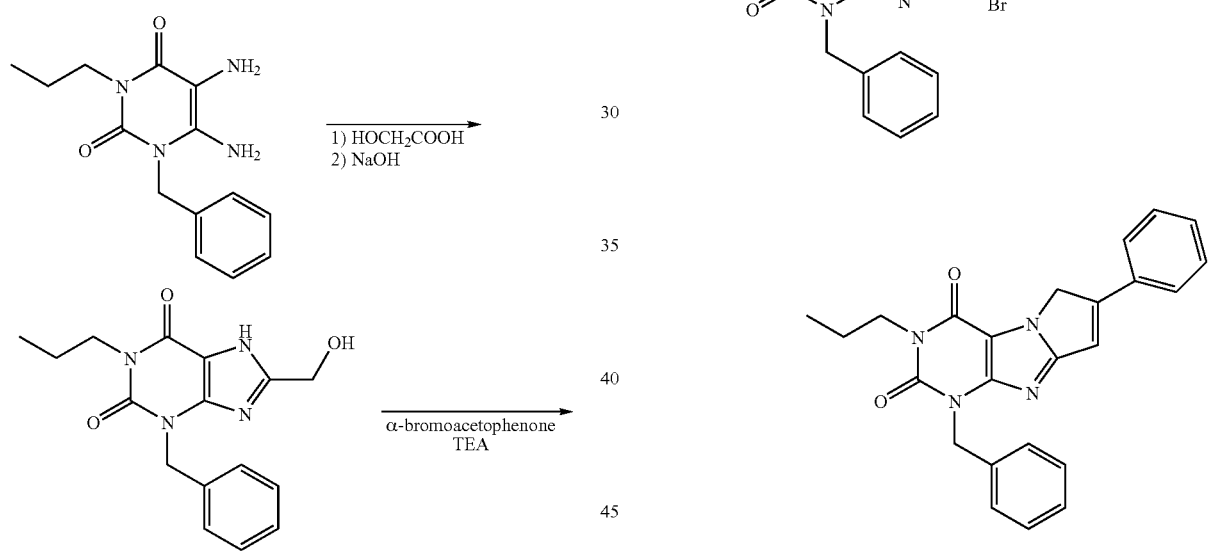

Scheme 3

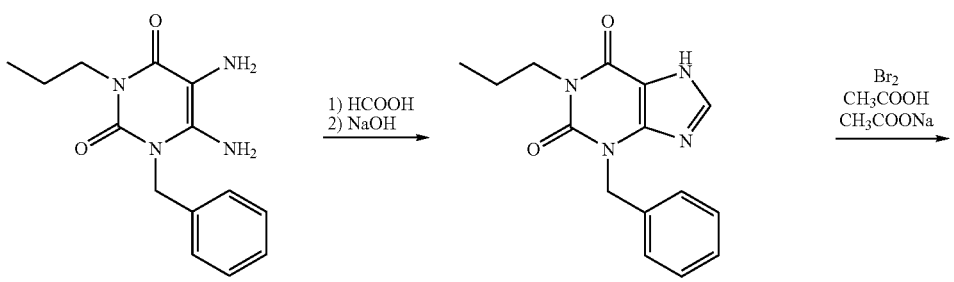

11                                    12
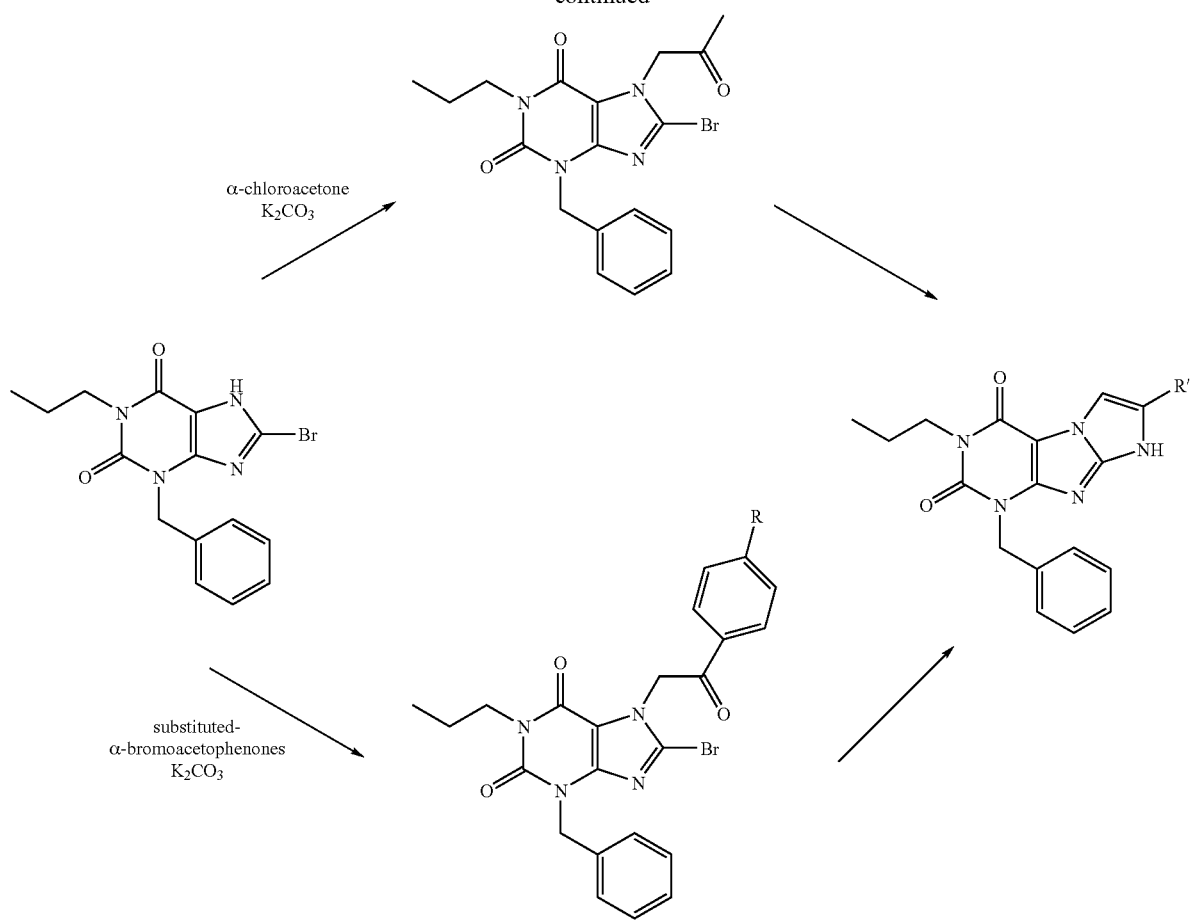
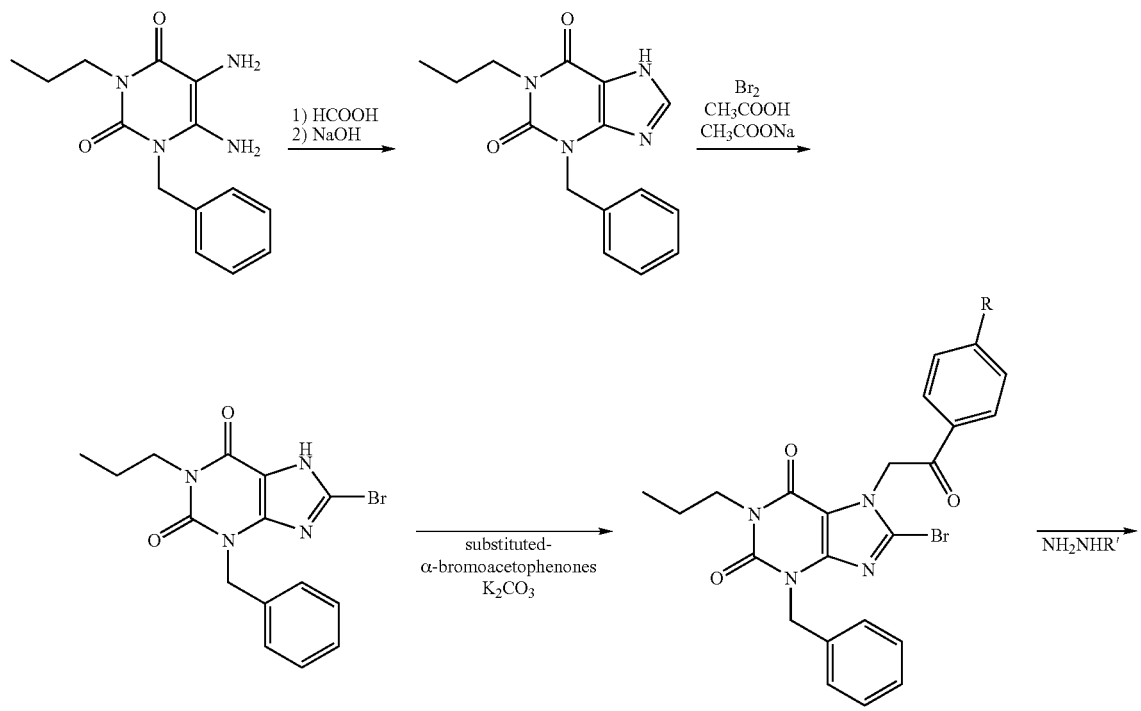

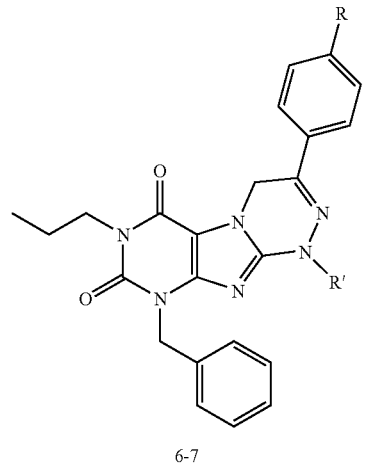

6-7

Furthermore, certain compounds of the present invention may be prepared as illustrated in Scheme 5 starting from, e.g., 1,3-dimethyl-8-nitro-1H-purine-2,6(3H,9H)-dione.

Scheme 5a

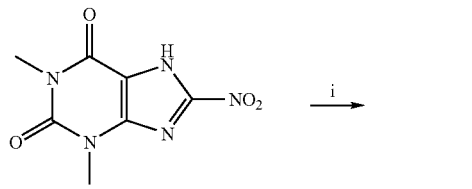

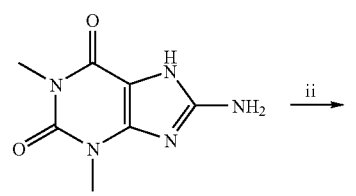

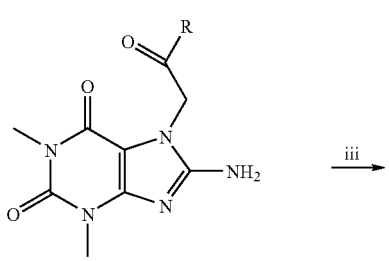

R = Ph
R = 4-OCH$_3$—Ph
R = 4-F—Ph
R = 4-Ph—Ph
R = 4-Cl—Ph
R = 4-Br—Ph
R = CH$_3$

-continued

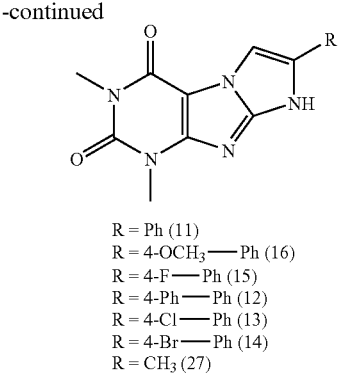

R = Ph (11)
R = 4-OCH$_3$—Ph (16)
R = 4-F—Ph (15)
R = 4-Ph—Ph (12)
R = 4-Cl—Ph (13)
R = 4-Br—Ph (14)
R = CH$_3$ (27)

[a] Reagents: (i) NH$_2$NH$_2$, 10% C/Pd, CH$_3$OH; (ii) α-halo-ketone, K$_2$CO$_3$, DMF, rt, 4-6 h; (iii) CH$_3$COOH, reflux, 4 h.

The present invention also encompasses the use of the disclosed compounds in screening assays to determine the effectiveness of other compounds for binding to the A$_3$ adenosine receptor through competitive inhibition as determined by various binding assays. Such a screening assay can make use of a labeled form of one of the compounds, preferably tritiated. Such screening assays are described in Jacobson and Van Rhee, *Purinergic approaches to experimental therapy*, Jacobson and Jarvis, ed., Wiley, New York, 1997, pp. 101-128; Mathot et al., Brit. J. Pharmacol., 116: 1957-1964 (1995); van der Wenden et al., J. Med. Chem., 38: 4000-4006 (1995); and van Calenbergh, J. Med. Chem., 40:3765-3772 (1997), the contents of which are hereby incorporated by reference.

In preferred embodiments, the compounds of the invention are adenosine antagonists possessing A$_3$ receptor affinity in the low nanomolar range, e.g., having a K$_i$ (hA$_3$) value from binding assay of less than 100 nM, more preferably less than 10 nM, more preferably less than 5 nM, and still more preferably less than 1.0 nM. For example, as described below, 1-benzyl-7-methyl-3-propyl-1H-imidazo[1,2-f]purine-2,4 (3H,8H)-dione (Compound 10) shows a K$_i$ (hA$_3$) value from binding assay of about 0.8 nM. In certain preferred embodiments, a compound of the invention exhibits practically complete selectivity versus the other adenosine receptor subtypes, e.g., having selectivity ratios of K$_i$ (hA$_1$)/K$_i$ (hA$_3$) of about 3163, $K_i(hA_{2A})/K_i(hA_3)$ of about 6250, $IC_{50}(hA_{2B})/K_i(hA_3)$ of about 2570.

Certain preferred compounds of this invention are listed in Table 1.

TABLE 1

| Compound # | Structure | Name |
|---|---|---|
| 1 | 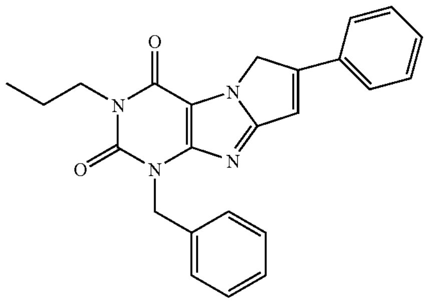 | 1-Benzyl-7-phenyl-3-propyl-1H-pyrrolo[1,2-f]purine-2,4(3H,6H)-dione |
| 2 | 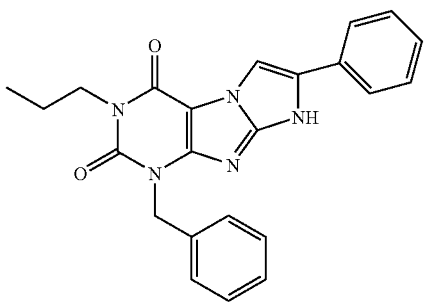 | 1-Benzyl-7-phenyl-3-propyl-1H-imidazo[1,2-f]purine-2,4(3H,8H)-dione |
| 3 | 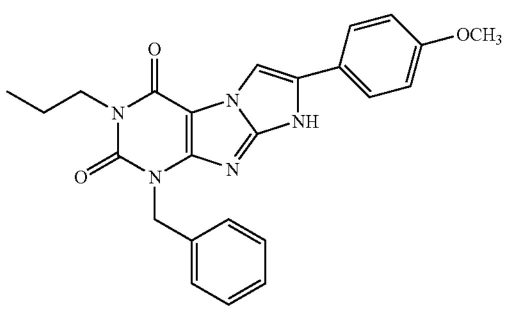 | 1-Benzyl-7-(4-methoxyphenyl)-3-propyl-1H-imidazo[1,2-f]purine-2,4(3H,8H)-dione |
| 4 | 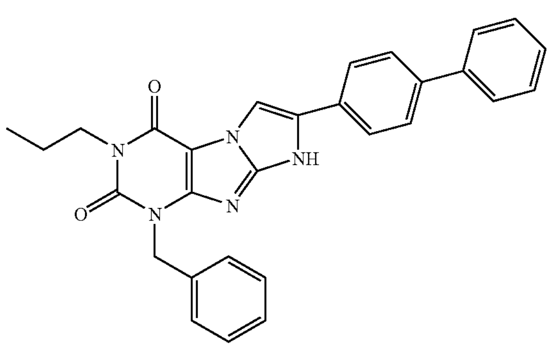 | 1-Benzyl-7-(biphenyl-4-yl)-3-propyl-1H-imidazo[1,2-f]purine-2,4(3H,8H)-dione |

TABLE 1-continued

| Compound # | Structure | Name |
|---|---|---|
| 5 | 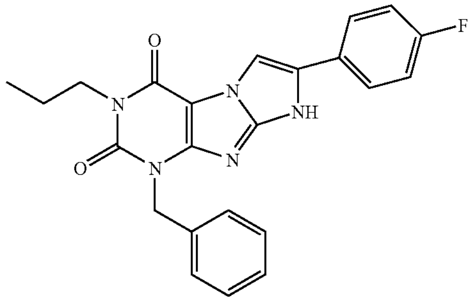 | 1-Benzyl-7-(4-fluorophenyl)-3-propyl-1H-imidazo[1,2-f]purine-2,4(3H,8H)-dione |
| 6 | 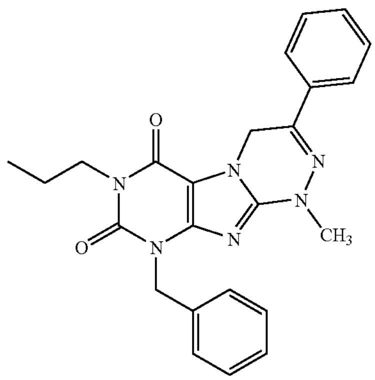 | 8-Benzyl-1-methyl-3-phenyl-6-propyl-1,4-dihydro-8H-1,2,4a,6,8,9-hexaaza-fluorene-5,7-dione |
| 7 | 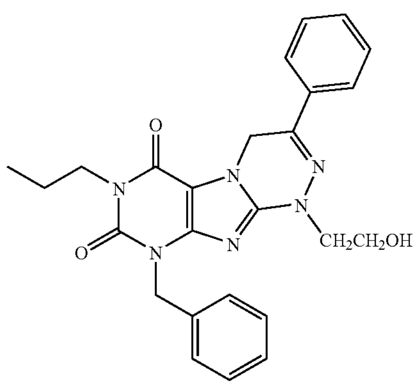 | 8-Benzyl-1-(2-hydroxy-ethyl)-3-phenyl-6-propyl-1,4-dihydro-8H-1,2,4a,6,8,9-hexaaza-fluorene-5,7-dione |
| 8 | 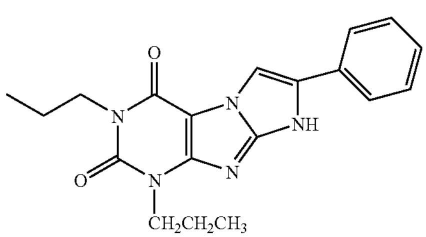 | 7-Phenyl-1,3-dipropyl-1H-imidazo[1,2-f]purine-2,4(3H,8H)-dione |
| 9 | 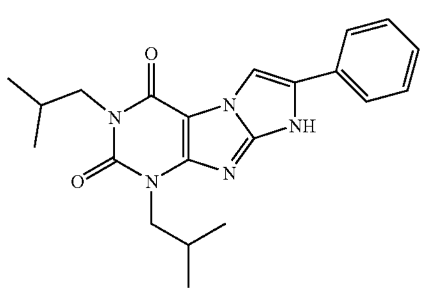 | 1,3-Diisobutyl-7-phenyl-1H-imidazo[1,2-f]purine-2,4(3H,8H)-dione |

TABLE 1-continued
| Compound # | Structure | Name |
| --- | --- | --- |
| 10 | 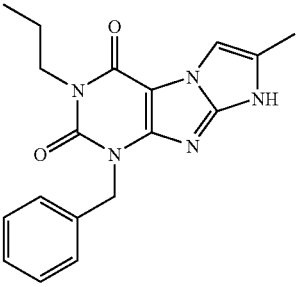 | 1-Benzyl-7-methyl-3-propyl-1H-imidazo[1,2-f]purine-2,4(3H,8H)-dione |
| 11 | 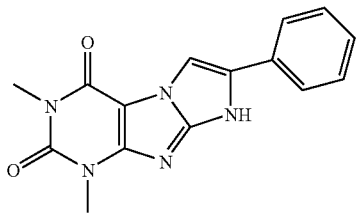 | 1,3-Dimethyl-7-phenyl-1H-imidazo[1,2-f]purine-2,4(3H,8H)-dione |
| 12 | 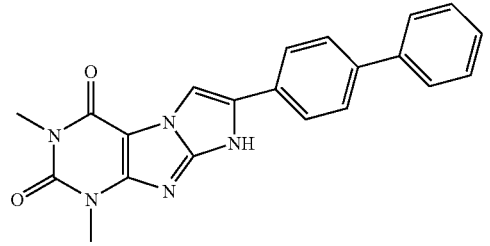 | 7-(Biphenyl-4-yl)-1,3-dimethyl-1H-imidazo[1,2-f]purine-2,4(3H,8H)-dione |
| 13 | 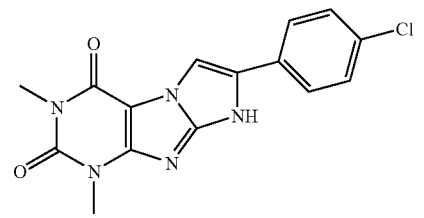 | 7-(4-Chlorophenyl)-1,3-dimethyl-1H-imidazo[1,2-f]purine-2,4(3H,8H)-dione |
| 14 | 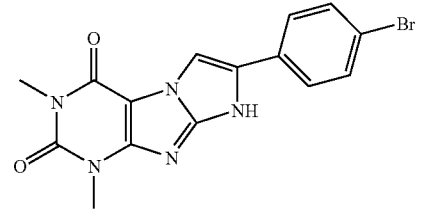 | 7-(4-Bromophenyl)-1,3-dimethyl-1H-imidazo[1,2-f]purine-2,4(3H,8H)-dione |
| 15 | 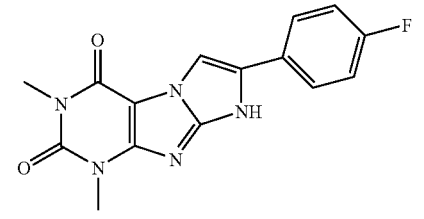 | 7-(4-Fluorophenyl)-1,3-dimethyl-1H-imidazo[1,2-f]purine-2,4(3H,8H)-dione |

TABLE 1-continued

| Compound # | Structure | Name |
|---|---|---|
| 16 | 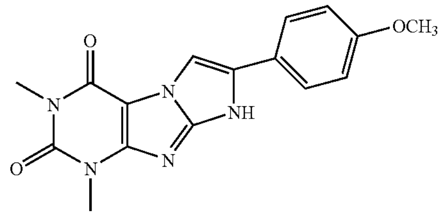 | 7-(4-Methoxyphenyl)-1,3-dimethyl-1H-imidazo[1,2-f]purine-2,4(3H,8H)-dione |
| 17 | 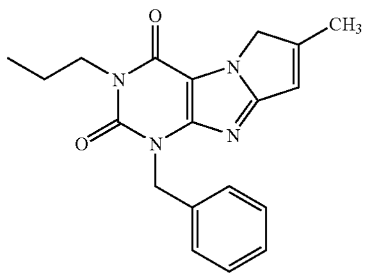 | 1-Benzyl-7-methyl-3-propyl-1H-pyrrolo[1,2-f]purine-2,4(3H,6H)-dione |
| 18 | 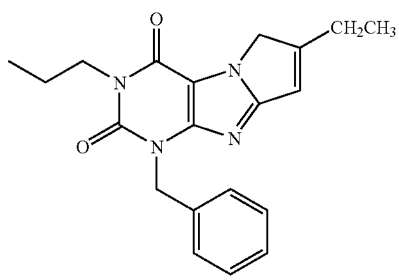 | 1-Benzyl-7-ethyl-3-propyl-1H-pyrrolo[1,2-f]purine-2,4(3H,6H)-dione |
| 19 | 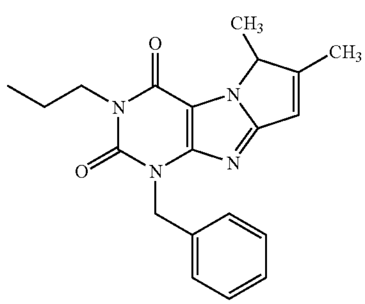 | 1-Benzyl-6,7-dimethyl-3-propyl-1H-pyrrolo[1,2-f]purine-2,4(3H,6H)-dione |
| 20 | 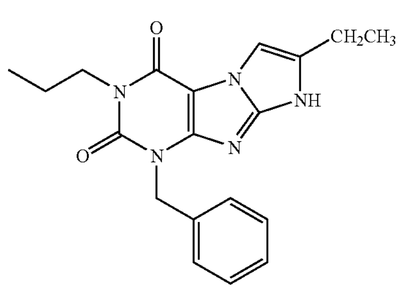 | 1-Benzyl-7-ethyl-3-propyl-1H-imidazo[1,2-f]purine-2,4(3H,8H)-dione |

TABLE 1-continued
| Compound # | Structure | Name |
|---|---|---|
| 21 | 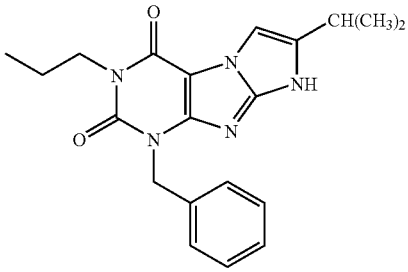 | 1-Benzyl-7-isopropyl-3-propyl-1H-imidazo[1,2-f]purine-2,4(3H,8H)-dione |
| 22 | 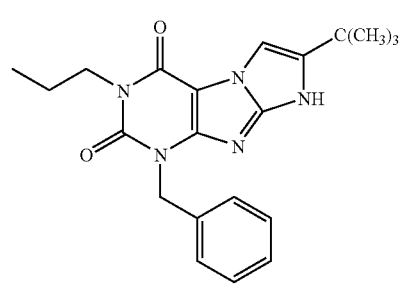 | 1-Benzyl-7-tert-butyl-3-propyl-1H-imidazo[1,2-f]purine-2,4(3H,8H)-dione |
| 23 | 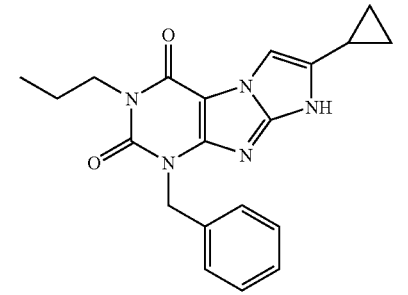 | 1-Benzyl-7-cyclopropyl-3-propyl-1H-imidazo[1,2-f]purine-2,4(3H,8H)-dione |
| 24 | 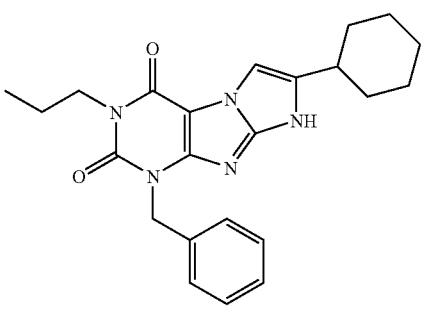 | 1-Benzyl-7-cyclohexyl-3-propyl-1H-imidazo[1,2-f]purine-2,4(3H,8H)-dione |
| 25 | 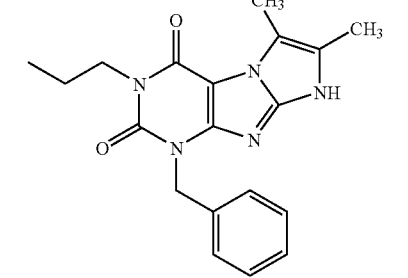 | 1-Benzyl-6,7-dimethyl-3-propyl-1H-imidazo[1,2-f]purine-2,4(3H,8H)-dione |

TABLE 1-continued

| Compound # | Structure | Name |
|---|---|---|
| 26 | 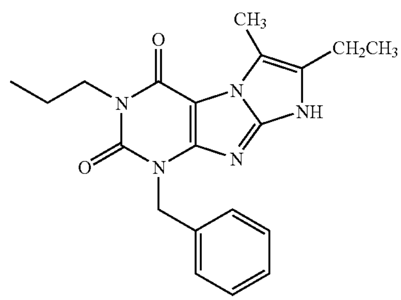 | 1-Benzyl-7-ethyl-6-methyl-3-propyl-1H-imidazo[1,2-f]purine-2,4(3H,8H)-dione |
| 27 | 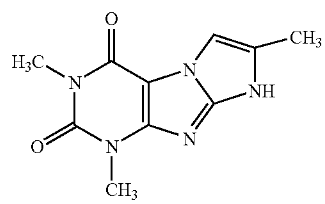 | 1,3,7-Trimethyl-1H-imidazo[1,2-f]purine-2,4(3H,8H)-dione |

Methods for the Treatment of Medical Conditions.

Also provided by this invention are methods of using the disclosed compounds for the treatment of various medical conditions.

The compounds provided by this invention are potent modulators of the $A_3$ adenosine receptor. The $A_3$ adenosine receptor is thought to mediate many processes, such as inflammation, and mast cell degranulation. The $A_3$ receptor is believed to also play a role in the central nervous system. Mediation of the $A_3$ receptor seems to induce behavioral depression and protect against cerebral ischemia. Further, mediation of the $A_3$ adenosine receptor is also thought to induce apoptosis in HL-60 human leukemia cells.

Thus, methods for the treatment of diseases that are mediated by the $A_3$ receptor are encompassed by this invention. This would include methods for the treatment of behavioral depression, cerebral ischemia, leukemia, inflammation and inflammatory diseases such as asthma, chemically induced seizures, cardioprotection, and ischemic heart preconditioning. The compounds of this invention can also be used as therapeutic agents in regulating cell growth, inducing apoptosis, and controlling the abnormal growth of certain tumors expressing the $A_3$ adenosine receptor.

Use of these compounds in methods to treat cancer is also encompassed. This includes cancers that express elevated levels of $A_3$ receptors. These cancers would include, but not be limited to, solid tumors, including ovarian cancer, breast cancer, colon cancer, lung cancer, pancreatic cancer and melanoma.

The compounds and/or pharmaceutical compositions of the invention are administered to a subject in amounts effective to treat or prevent a condition (e.g., cancer). In preferred embodiments, a compound of the invention is administered at a dosage of between 0.01 and 100 mg/kg/day, more preferably less than about 10 mg/kg/day, more preferably less than about 5 mg/kg/day, more preferably less than about 1 mg/kg/day, more preferably less than about 0.5 mg/kg/day, and more preferably less than about 0.1 mg/kg/day. In certain embodiments, the compound of the invention is administered at a dosage of at least 0.01 mg/kg/day, about 0.05 mg/kg/day, about 0.1 mg/kg/day, about 0.5 mg/kg/day, about 1.0 mg/kg/day, or about 10 mg/kg/day.

Two or more compounds and/or pharmaceutical compositions of the invention can also be administered simultaneously or sequentially to a subject administered to a subject to achieve a therapeutic effect. Further, the compounds and/or pharmaceutical compositions of the invention can be administered together with other active ingredients.

EXAMPLES

These examples are intended as preferred embodiments only, and are provided to further illustrate this invention. They are not intended, either individually, in combination, or collectively, to define the full scope of this invention.

Binding Assay Methodology.

The expression of the human $A_1$, $A_{2A}$ and $A_3$ receptors in CHO cells is described in Klotz et al., Naunyn Schmied. Arch. Pharmacol. 357: 1-9, (1998). The cells were grown adherently and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G418, 0,2 mg/mL) at 37° C. in 5% CO2/95% air. Cells were split 2 or 3 times weekly at a ratio between 1:5 and 1:20. For membrane preparation the culture medium was removed and the cells were washed with PBS and scraped off T75 flasks in ice-cold hypotonic buffer (5 mM Tris HCl, 2 mM EDTA, pH 7.4).

The cell suspension was homogenized with Polytron and the homogenate was spun for 10 min at 1,000×g. The supernatant was then centrifuged for 30 min at 100,000×g. The membrane pellet was resuspended in 50 mM Tris HCl buffer pH 7.4 (for $A_3$ adenosine receptors: 50 mM Tris HCl, 10 mM MgCl2, 1 mM EDTA) and incubated with 3 UI/mL of Adenosine deaminase for 30 min at 37° C. Then the suspension was frozen at −80° C. HEK 293 cells transfected with the human recombinant A2B adenosine receptor were obtained from Receptor Biology, Inc. (Beltsville, Md., USA).

Binding of [³H]-DPCPX to CHO cells transfected with the human recombinant A₁ adenosine receptor was performed according to the method described by Klotz et al., J. Biol. Chem., 260, 14659-14664, (1985). Displacement experiments were performed for 120 min at 25° C. in 0.2 mL of 50 mM Tris HCl buffer pH 7.4 containing 1 nM [³H]-DPCPX, diluted membranes (50 μg of protein/assay) and at least 6-8 different concentrations of antagonists studied. Non-specific binding was determined in the presence of 10 μM of CHA and this was always ≦10% of the total binding.

Binding of [³H]-SCH 58261 to CHO cells transfected with the human recombinant $A_{2A}$ adenosine receptors (50 μg of protein/assay) was performed using 0.2 mL 50 mM Tris HCl buffer, 10 mM MgCl₂ pH 7.4 and at least 6-8 different concentrations of antagonists studied for an incubation time of 30 min at 25° C. Non-specific binding was determined in the presence of 50 μM NECA and was about 20% of total binding.

Competition experiments of [³H]-DPCPX to HEK-293 cells transfected with the human recombinant $A_{2B}$ adenosine receptor were performed for 60 min at 25° C. in 0.1 mL of 50 mM Tris HCl buffer, 10 mM MgCl₂, 1 mM EDTA, 0.1 mM benzamidine pH 7.4, 2 IU/mL adenosine deaminase containing 34 nM [³H]-DPCPX, diluted membranes (20 μg of protein/assay) and at least 6-8 different concentrations of selected compounds. Non-specific binding was determined in the presence of 100 μM of NECA and was always ≦30% of the total binding.

Binding of [³H]-MRE 3008F20 to CHO cells transfected with the human recombinant A₃ adenosine receptors was performed according to Varani et al., 2000. Competition experiments were carried out in duplicate in a final volume of 100 μl in test tubes containing 1 nM [³H]-MRE 3008F20, 50 mM Tris HCl buffer, 10 mM MgCl₂, 1 mM EDTA pH 7.4 and 100 μl of diluted membranes (50 μg of protein/assay) and at least 8-10 different concentrations of examined antagonists. Incubation time was 120 min at 4° C., according to the results of previous time-course experiments. Non-specific binding was defined as binding in the presence of 1 μM MRE 3008F20 and was about 30% of total binding.

The filter bound radioactivity was counted on Top Count Microplate Scintillation Counter (efficiency 57%) with Micro-Scint 20. The protein concentration was determined with bovine albumin as a standard reference and according to the method described in Bradford, M. M. Anal. Biochem. 72, 248. Inhibitory binding constant, $K_i$, values were calculated from those of $IC_{50}$ according to the Cheng & Prusoff equation described in Cheng, Y. C. and Prusoff, W. H., Biochem. Pharmacol. 22: 3099-3108, (1973). Ki=IC50/(1+[C*]/KD*), where [C*] is the concentration of the radioligand and KD* its dissociation constant. A weighted non-linear least-squares curve fitting program LIGAND described in Munson, P. J. and Rodboard, D., Anal. Biochem. 107, 220-239, (1980) was used for computer analysis of inhibition experiments. Data are expressed as the geometric mean, with 95% or 99% confidence limits in parentheses.

Chemistry.

Reaction progress and product mixtures were monitored by thin-layer chromatography (TLC) on silica gel (procoated $F_{254}$ Merck plates) and visualized with aqueous potassium permanganate or a methanolic solution of ninhydrin. ¹H-NMR were determined in CDCl₃ or DMSO-d₆ solutions with a Bruker AC 200 spectrometer; peak positions are given in parts per million (δ) downfield from tetramethylsilane as internal standard and J values are given in Hertz. Light petroleum refers to the fractions boiling at 40-60° C. Melting points were determined on a Buchi-Tottoli instrument and are uncorrected. Chromatography was performed on Merck 230-400 mesh silica gel. Organic solutions were dried over anhydrous sodium sulfate.

Example 1

PREPARATION OF 1-BENZYL-6-AMINO-URACIL

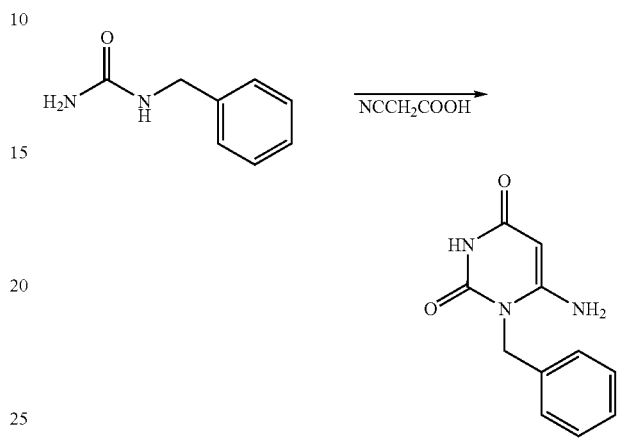

A mixture of benzylurea (33.3 mmol), 2-cyanoacetic acid (36.63 mmol) and Ac₂O (20 mL) was heated at 75-80° C. for 2 hours. After cooling to room temperature, 30 mL of Et₂O was added and the resultant suspension was stirred for 1 h. The solid intermediate was filtered, suspended in a mixture of water (30 mL) and ethanol (15 mL) and heated at 80-85° C. 5 mL of 10% NaOH were slowly added. After 30 minutes, the reaction mixture was concentrated, acidified with 10% HCl and the precipitate collected by filtration (Yellow solid. Yield 70-80%).

Example 2

PREPARATION OF 1-BENZYL-3-PROPYL-6-DIMETHYLAMINO-METHYLENEAMINO-URACIL

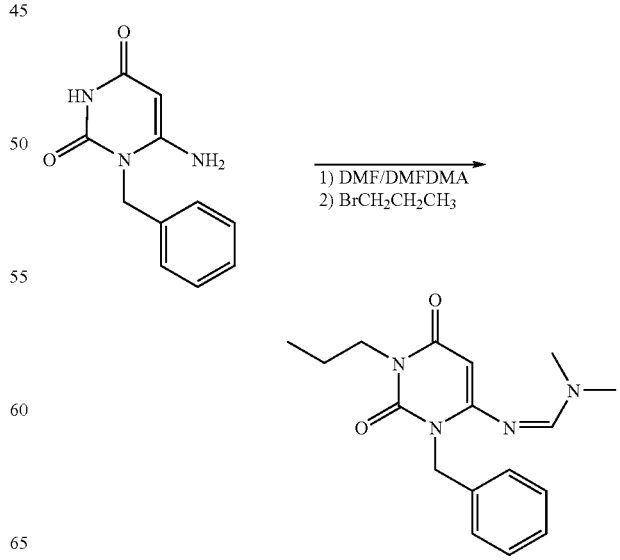

A solution of 1-benzyl-6-aminouracil (4.6 mmol) in anhydrous DMF (20 mL) and dimethylformamide dimethylacetal (DMFDMA) (18.4 mmol) was heated at 45° C. under stirring. After 1 hour $K_2CO_3$ (6.9 mmol) and 1-bromopropane (6.9 mmol) were added and the reaction was stirred at 80° C. overnight. The solvent was evaporated under vacuum to obtain a solid residue which was suspended with hot ethyl acetate (100 mL) and filtered with celite. The filtrate was evaporated and the product purified by crystallization with AcOEt. (Pale yellow solid. Yield 50%).

Example 3

PREPARATION OF 1-BENZYL-3-PROPYL-6-AMINO-URACIL

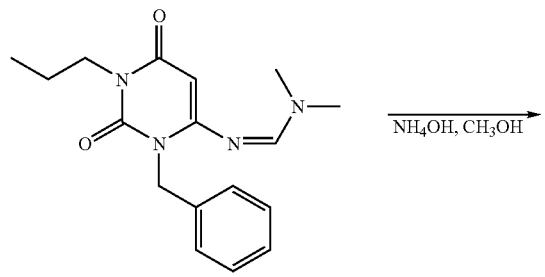

A solution of the dimethylamino-methylene derivative (1.9 mmol) in methanol (10 mL) and 30% $NH_4OH$ (25 mL) was stirred at room temperature for 3 days. The solvent was concentrated and the product precipitated as a white solid which was collected by filtration (White solid. Yield 90%).

Example 4

PREPARATION OF 1-BENZYL-3-PROPYL-5-NITROSO-6-AMINO-URACIL

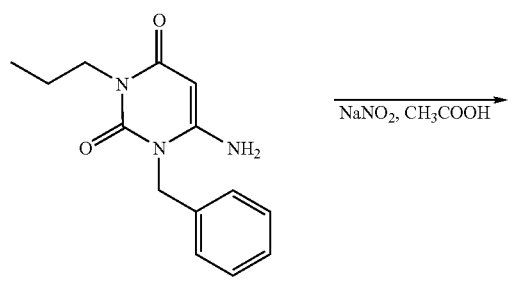

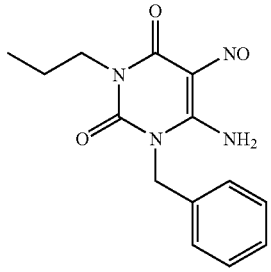

A solution of 1-benzyl-3-propyl-6-amino-uracil (6.2 mmol) in 80% acetic acid (15 mL) and 30 mL of ethanol, was stirred at 40° C. while a solution of $NaNO_2$ (9.3 mmol) in water (10 mL) was added drop wise. The reaction was stirred for 30 minutes at 40° C. and after concentration the product precipitated from the reaction mixture and was collected by filtration. (Pink solid. Yield 85%).

Example 5

PREPARATION OF 1-BENZYL-3-PROPYL-5,6-DIAMINO-URACIL

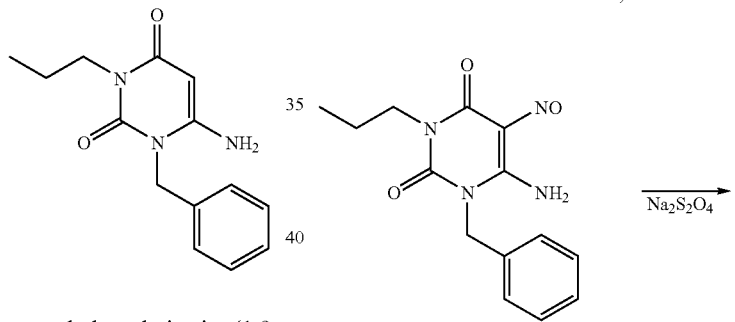

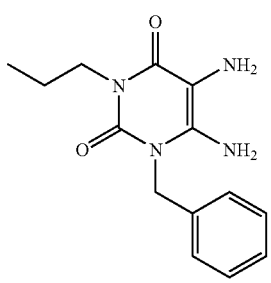

A solution of the nitroso-uracil derivative (from Example 4) (5 mmol) in water (25 mL) and 30% $NH_4OH$ (10 mL) was heated at 85° C. and sodium dithionite (15 mmol) was added in small portions under vigorous stirring until the red color disappeared (15-30 minutes). The reaction was then cooled and the mixture extracted with ethyl acetate. The organic phase was dried with $Na_2SO_4$, evaporated under vacuum and the product purified by crystallization with ethyl acetate or ethanol. (Pale yellow solid. Yield 45%).

Example 6

PREPARATION OF 1-PROPYL-3-BENZYL-8-HYDROXYMETHYL-XANTHINE

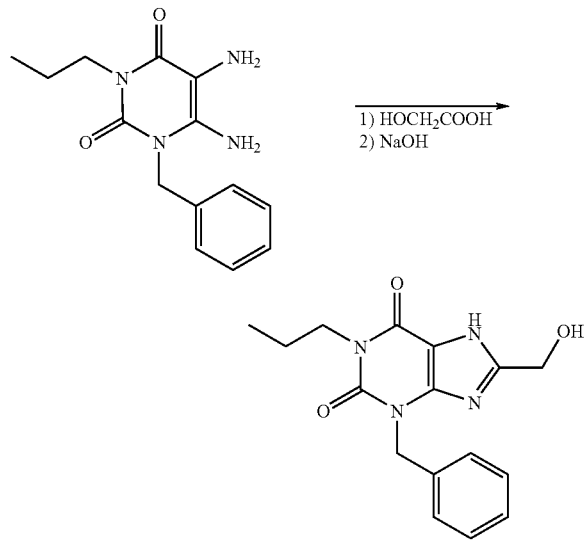

A mixture of the diamino-uracil derivative (from Example 5) (3.6 mmol), glycolic acid (7.3 mmol) and 1,4-dioxane (1 mL) was heated at 100° C. for 1 h. After cooling, a yellow solid precipitated from the solution and it was suspended in a mixture of H$_2$O/EtOH 1:1 (20 mL). After basification with NaOH, the solution was heated at reflux for 3 hours, then cooled to 0° C. and acidified with acetic acid. The product precipitated as a white solid which was collected by filtration and dried. (White solid. Yield 70%).

Example 7

PREPARATION OF 1-PROPYL-3-BENZYL-7-(2-OXO-2-PHENYL-ETHYL)-8-HYDROXYM-ETHYL-XANTHINE

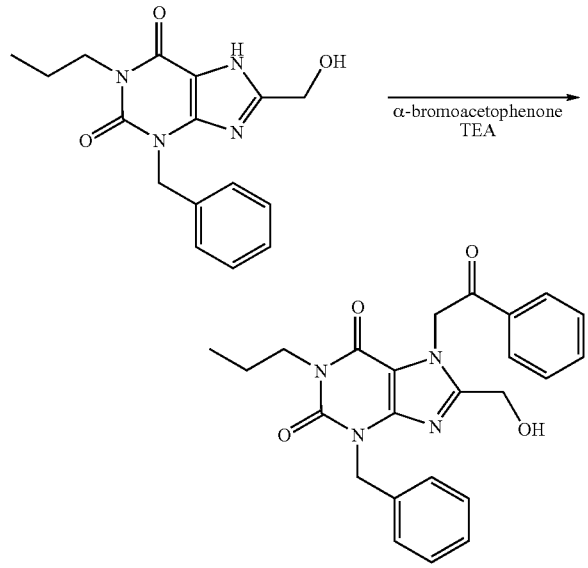

The starting xanthine derivative (from Example 6) (2.07 mmol) was suspended in water (10 mL) and TEA (2.07 mmol) and the suspension was stirred at room temperature while a solution of α-bromoacetophenone (2.5 mmol) in THF (5 mL) was slowly added. The reaction was stirred at room temperature over night then concentrated and extracted with ethyl acetate. The organic phase was dried with sodium sulfate and evaporated to obtain a solid residue which was purified by crystallization with ethanol. (White solid. Yield 80%).

Analogous compounds were prepared by a similar general procedure: The 3-benzyl-8-hydroxymethyl-1-propyl-3,7-dihydro-purine-2,6-dione (1 mmol) was dissolved in anhydrous DMF (5 mL) and anhydrous K$_2$CO$_3$ (2 mmol) was added. After stirring for 5 minutes at room temperature, a solution of the appropriate α-halo-ketone (1 mmol) in DMF (2 mL) was slowly added. The reaction was stirred at room temperature monitoring the course by TLC (6-10 hrs) then the solvent was evaporated and the residue suspended with water and extracted with EtOAc (3×100 mL). The combined organic layers were dried with anhydrous sodium sulfate and evaporated to dryness.

Example 8

PREPARATION OF 1-PROPYL-3-BENZYL-7-(2-OXO-2-PHENYL-ETHYL)-8-BROMOMETHYL-XANTHINE

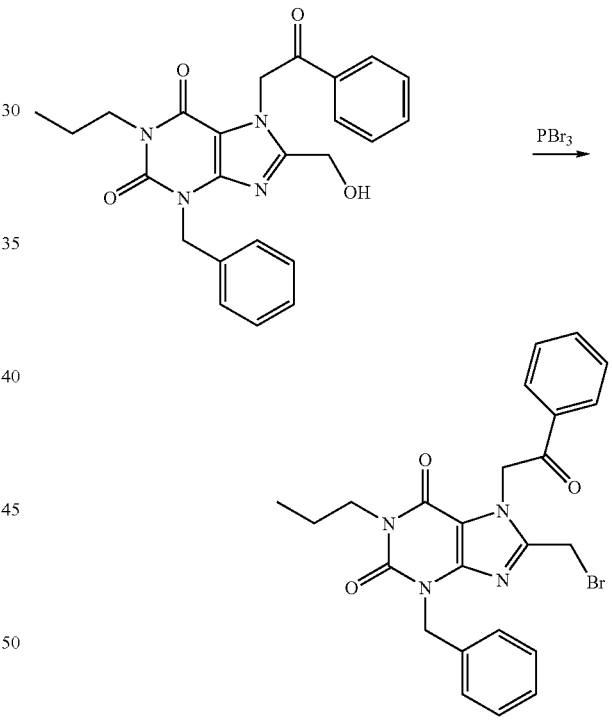

The starting xanthine derivative (from Example 7) (1.52 mmol) was dissolved in anhydrous benzene (40 mL) and to the solution was added PBr$_3$ (5 eq) drop wise with stirring. The mixture was stirred at room temperature for 4 hours and the product precipitated from the reaction mixture as a yellow solid. To the suspension was added ethyl acetate and the organic layer was washed with water and dried with sodium sulfate. The solvent was evaporated to obtain a solid residue which was suspended with a mixture of Et$_2$O/hexane and filtered. (White solid. Yield 85%).

Analogous compounds were prepared by a similar general procedure. The appropriate 3-benzyl-8-hydroxymethyl-7-(2-oxo-alkyl)-1-propyl-3,7-dihydro-purine-2,6-dione derivatives (1.52 mmol) were dissolved in anhydrous benzene (25 mL) and PBr$_3$ (7.6 mmol) was added drop wise at room temperature under stirring. The mixture was stirred for further 4-6 h at room temperature then the solvent was evaporated and the residue suspended with water and extracted with EtOAc (3×100 mL). The combined organic layers were evaporated after drying with anhydrous sodium sulfate. Compounds were used without further purification or were purified by crystallization or column chromatography.

Example 9

PREPARATION OF COMPOUND 1
(INTRAMOLECULAR WITTIG REACTION)

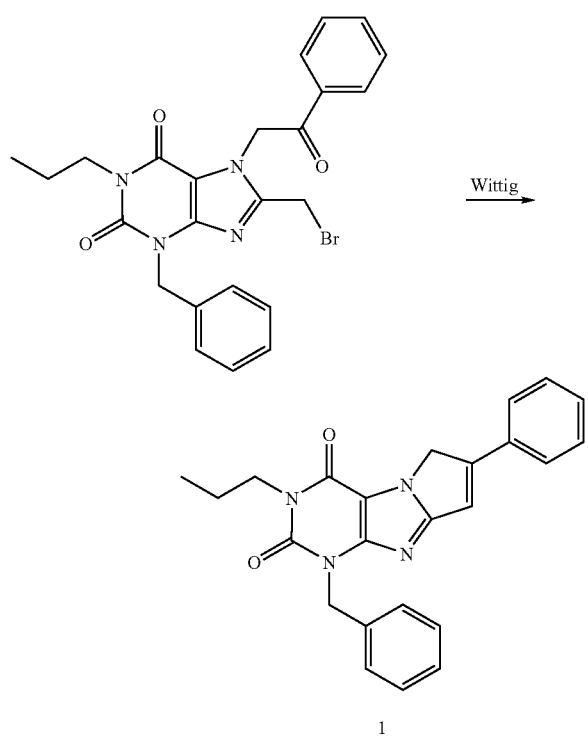

A mixture of the starting bromo-derivative from Example 8 (0.42 mmol) and PPh$_3$ (0.46 mmol) in anhydrous benzene (5 mL) was refluxed for 5 hours. The solvent was evaporated to give a solid residue which was crystallized from AcOEt-Et$_2$O. (White solid. Yield 85%). A solution of the resultant phosphonium salt (0.26 mmol) in methanol (5 mL) was cooled at 0° C. and MeO—Na+ (0.28 mmol) was added. The reaction mixture was stirred at 0° C. for 5 minutes and finally at room temperature for further 5 minutes. The solvent was evaporated and the residue purified by column chromatography (AcOEt/Petroleum ether 1:4). (White solid. Yield 85%).

Analogous intramolecular Wittig reactions were performed using a similar general procedure to prepare Compounds 17, 18 and 19: A solution of the corresponding bromide (0.42 mmol) and PPh$_3$ (0.46 mmol) in anhydrous benzene (5 mL) was refluxed for 5 h. After this time, the resulting mixture was concentrated to half-volume and the precipitates collected by filtration. The intermediate phosphonium salts (0.26 mmol) were then added to an ice-cooled and stirred solution of sodium methoxide (0.29 mmol) in anhydrous methanol (5 mL). The reaction was stirred at 0° C. for 10 minutes; then the solvent was evaporated and the products purified by column chromatography on silica gel.

Example 10

PREPARATION OF
1-PROPYL-3-BENZYL-XANTHINE

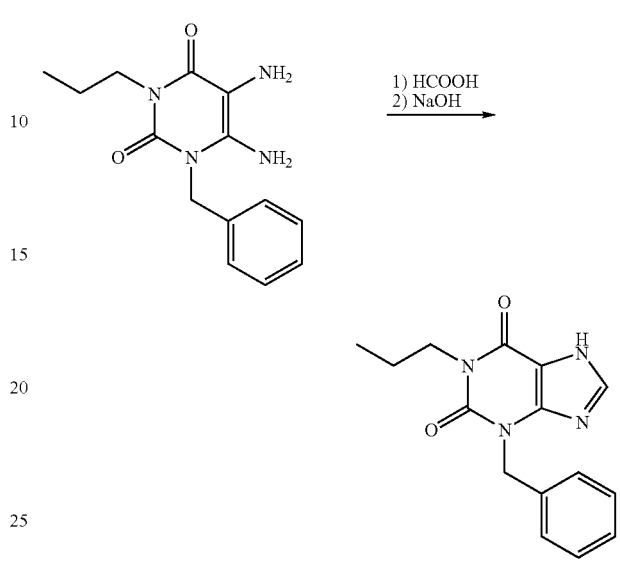

The diamino derivative (3.28 mmol) was dissolved in formic acid (15 mL) and the solution was refluxed for 1 hour. The excess of acid was evaporated and the residue suspended in 10% NaOH (15 mL) and EtOH (5 mL). The mixture was heated at reflux for 1 hour then concentrated. After cooling at 0° C. the product was precipitated by acidification with 20% HCL (White solid. Yield 90%).

Example 11

PREPARATION OF
1-PROPYL-3-BENZYL-8-BROMO-XANTHINE

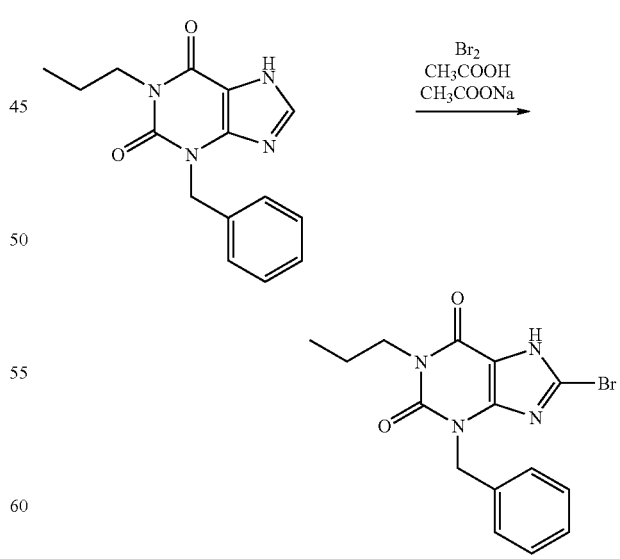

A mixture of 1-propyl-3-benzyl xanthine (2.82 mmol), CH$_3$CO$_2$Na (2.82 mmol) and acetic acid (15 mL) was heated at 40-50° C. To the solution was added Br$_2$ (2.82 mmol) and the reaction was stirred for further 30 minutes at 45° C. After cooling at room temperature the precipitate was collected by filtration and finally crystallized from EtOH. (White solid. Yield 85%).

Example 12

REPRESENTATIVE GENERAL PROCEDURE FOR THE PREPARATION OF 3-BENZYL-8-BROMO-7-(2-OXO-PROPYL)-1-PROPYL-3,7-DIHYDRO-PURINE-2,6-DIONE AND ANALOGS

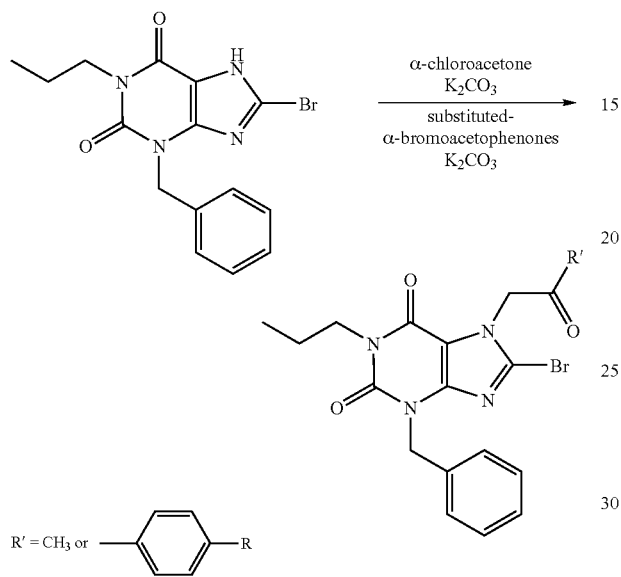

The 3-benzyl-8-bromo-1-propyl-3,7-dihydro-purine-2,6-dione (0.55 mmol) was dissolved in anhydrous DMF (4 mL) and anhydrous K$_2$CO$_3$ (1.1 mmol) was added. After stirring for 5 minutes at room temperature, a solution of the appropriate α-Br/Cl ketone (0.55 mmol) in DMF (2 mL) was slowly added. The reaction was stirred at room temperature monitoring the course by TLC (2-10 hrs) then the solvent was evaporated and the residue suspended with water and extracted with AcOEt (3×50 mL). The combined organic layers were dried with anhydrous sodium sulfate and evaporated to dryness.

Example 13

Representative General Procedure for the Preparation of Compounds 6 and 7

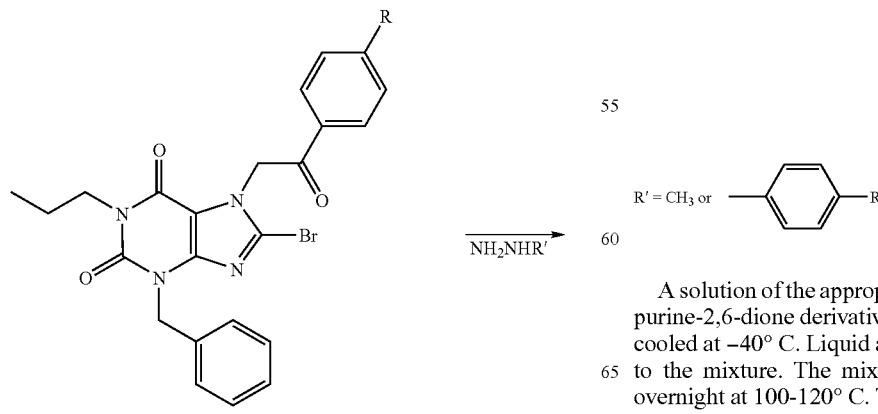

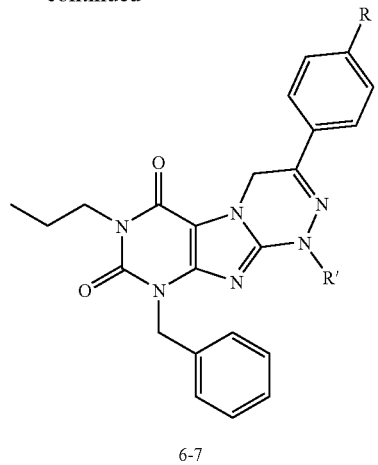

6-7

A mixture of the desired 7-substituted purine-2,6-dione derivative from Example 12 (0.073 mmol), N-hydroxyethyl-hydrazine or N-methyl-hydrazine (0.15 mmol) and TEA (0.073 mmol) in ethanol (3 mL) was heated in a steel bomb at 120° C. for 24 hours. The solvent was evaporated and the residue purified by crystallization with ethanol. (Yield 80-85%).

Example 14

Representative General Procedure for the Preparation of Compounds 2-5, 10 and 20-26

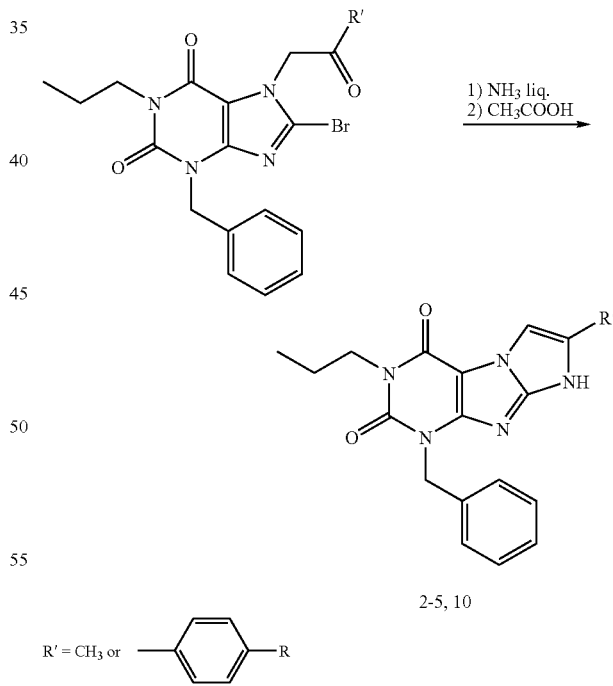

2-5, 10

A solution of the appropriate 7-(2-oxo-alkyl)-3,7-dihydro-purine-2,6-dione derivative (0.4 mmol) in EtOH (4 mL) was cooled at −40° C. Liquid ammonia (3-4 mL) was then added to the mixture. The mixture was heated in a sealed tube overnight at 100-120° C. The reaction was finally allowed to cool at room temperature then the solvent and the excess of ammonia were evaporated to obtain a residue which was suspended with water and extracted with EtOAc (3×25 mL). The organic phase was dried with anhydrous sodium sulfate and the solvent was evaporated to give a residue which was purified by column chromatography on silica gel eluting with the appropriate mixture of light petroleum-EtOAc.

Examples 15-26

Synthesis of Compounds 2-5, 10, and 20-26

Following the general procedure of Example 14, compounds 2-5, 10, and 20-26 were prepared.

1-Benzyl-7-phenyl-3-propyl-1H-imidazo[1,2-f]purine-2,4(3H,8H)-dione (Compound 2): white solid; 80% yield; mp 255° C.; $^1$H-NMR (DMSO-$d_6$, 200 MHz): δ 0.88 (t, 3H, J=7.6), 1.58 (m, 2H), 3.88 (t, 2H, J=7.2), 5.20 (s, 2H), 7.52-7.82 (m, 10H), 8.12 (s, 1H), 13.00 (bs, 1H).

1-Benzyl-7-(4-methoxyphenyl)-3-propyl-1H-imidazo[1,2-f]purine-2,4(3H,8H)-dione (Compound 3): white solid; 70% yield; mp 257° C.; $^1$H-NMR (DMSO-$d_6$, 400 MHz): δ 0.87 (t, 3H, J=7.6), 1.58 (m, 2H), 3.78 (s, 3H), 3.87 (t, 2H, J=7.2), 5.19 (s, 2H), 7.00 (d, 2H, J=8.8), 7.25-7.39 (m, 5H), 7.71 (d, 2H, J=8.8), 7.93 (s, 1H), 13.00 (bs, 1H).

1-Benzyl-7-(biphenyl-4-yl)-3-propyl-1H-imidazo[1,2-f]purine-2,4(3H,8H)-dione (Compound 4): white solid; 83% yield; mp 272° C.; $^1$H-NMR (CDCl$_3$, 400 MHz): δ 0.90 (t, 3H, J=7.6), 1.55 (m, 2H), 3.87 (t, 2H, J=7.2), 5.24 (s, 2H), 7.23-7.62 (m, 15H), 12.34 (bs, 1H).

1-Benzyl-7-(4-fluorophenyl)-3-propyl-1H-imidazo[1,2-f]purine-2,4(3H,8H)-dione (Compound 5): white solid; 50% yield; mp 250° C.; $^1$H-NMR (DMSO-$d_6$, 400 MHz): δ 0.87 (t, 3H, J=7.6), 1.60 (m, 2H), 3.90 (t, 2H, J=7.2), 5.19 (s, 2H), 7.20-8.00 (m, 10H), 13.00 (bs, 1H).

1-Benzyl-7-methyl-3-propyl-1H-imidazo[1,2-f]purine-2,4(3H,8H)-dione (Compound 10): white solid, 90% yield; mp 255° C.; $^1$H-NMR (DMSO-$d_6$, 400 MHz): δ 0.85 (t, 3H, J=7.8), 1.58 (m, 2H), 2.30 (s, 3H), 3.84 (t, 2H, J=7.6), 5.18 (s, 2H), 7.60-7.90 (m, 5H), 12.20 (bs, 1H).

1-Benzyl-7-ethyl-3-propyl-1H-imidazo[1,2-f]purine-2,4(3H,8H)-dione (Compound 20): white solid; 65% yield; mp 285° C.; $^1$H-NMR (DMSO-$d_6$, 200 MHz): δ 0.85 (t, 3H, J=7.6), 1.21 (t, 3H, J=7.4), 1.55 (m, 2H), 2.60 (m, 2H), 3.84 (t, 2H, J=7.2), 5.16 (s, 2H), 7.30 (m, 6H), 12.50 (bs, 1H).

1-Benzyl-7-isopropyl-3-propyl-1H-imidazo[1,2-f]purine-2,4(3H,8H)-dione (Compound 21): white solid; 78% yield; mp 128-130° C.; $^1$H-NMR (DMSO-$d_6$, 400 MHz): δ 0.85 (t, 3H, J=7.6), 1.24 (d, 6H, J=6.8), 1.56 (m, 2H), 2.89 (m, 1H), 3.84 (t, 2H, J=7.2), 5.16 (s, 2H), 7.24 (m, 6H), 12.40 (bs, 1H).

1-Benzyl-7-tert-butyl-3-propyl-1H-imidazo[1,2-f]purine-2,4(3H,8H)-dione (Compound 22): white solid; 58% yield; mp 230° C.; $^1$H-NMR (DMSO-$d_6$, 200 MHz): δ 0.85 (t, 3H, J=7.6), 1.29 (s, 9H), 1.56 (m, 2H), 3.85 (t, 2H, J=7.2), 5.17 (s, 2H), 7.14 (s, 1H), 7.30 (m, 5H), 12.40 (bs, 1H).

1-Benzyl-7-cyclopropyl-3-propyl-1H-imidazo[1,2-f]purine-2,4(3H,8H)-dione (Compound 23): white solid; 66% yield; mp 244-245° C.; $^1$H-NMR (DMSO-$d_6$, 200 MHz): δ 0.75 (m, 7H), 1.53 (m, 2H), 1.89 (m, 1H), 3.83 (t, 2H, J=7.2), 5.15 (s, 2H), 7.29 (m, 6H), 12.20 (bs, 1H).

1-Benzyl-7-cyclohexyl-3-propyl-1H-imidazo[1,2-f]purine-2,4(3H,8H)-dione (Compound 24): white solid; 40% yield; mp 130-132° C.; $^1$H-NMR (DMSO-$d_6$, 200 MHz): δ 0.83 (t, 3H, J=7.4), 1.10-1.92 (m, 13H), 3.83 (t, 2H, J=7.6), 5.14 (s, 2H), 7.25 (m, 6H), 12.20 (bs, 1H).

1-Benzyl-6,7-dimethyl-3-propyl-1H-imidazo[1,2-f]purine-2,4(3H,8H)-dione (Compound 25): white solid; 78% yield; mp 259° C.; $^1$H-NMR (DMSO-$d_6$, 200 MHz): δ 0.83 (t, 3H, J=7.4), 1.54 (m, 2H), 2.15 (s, 3H), 3.81 (t, 2H, J=7.2), 5.13 (s, 2H), 7.27 (m, 5H), 12.20 (bs, 1H).

1-Benzyl-7-ethyl-6-methyl-3-propyl-1H-imidazo[1,2-f]purine-2,4(3H,8H)-dione (Compound 26): white solid; 73% yield; mp 230° C.; $^1$H-NMR (DMSO-$d_6$, 200 MHz): δ 0.85 (t, 3H, J=7.6), 1.15 (t, 3H, J=7.3), 1.55 (m, 2H), 2.56 (m, 5H), 3.84 (t, 2H, J=7.6), 5.16 (s, 2H), 7.30 (m, 5H), 12.20 (bs, 1H).

Example 27

Affinity and Selectivity at the $A_3$ Receptor

The compounds of this invention show good affinity at the $A_3$ receptor, and good selectivity versus the $A_1$ receptor. Results of radioligand binding assays displacing agonists with representative preferred compounds at human $A_1$, $A_{2A}$, $A_{2B}$, and $A_3$ adenosine receptors expressed in CHO cells are shown in Table 2.

TABLE 2

| Cmpd | [$^3$H] DPCPX binding to h$A_1$ | [$^3$H] ZM 241385 binding to h$A_{2A}$ receptors expressed in CHO cells $K_i$(nM) | cAMP assay in CHO h$A_{2B}$ IC$_{50}$ (nM) | [$^3$H] MRE3008F20 binding to h$A_3$ receptors expressed in CHO cells $K_i$ (nM) |
|---|---|---|---|---|
| 1 | >1000 (75%) | >1000 (99%) | — | 200 (134-297) |
| 2 | >1000 (83%) | >1000 (99%) | — | 115 (89-150) |
| 3 | >1000 (99%) | >1000 (99%) | — | 55 (28-104) |
| 4 | >1000 (95%) | >1000 (98%) | — | >1000 (90%) |
| 5 | >1000 (90%) | >1000 (97%) | — | 22 (19-26) |
| 6 | >1000 (79%) | >1000 (99%) | >1000 (94%) | >1000 (99%) |
| 7 | >1000 (91%) | >1000 (99%) | >1000 (83%) | >1000 (99%) |
| 8 | 373 (330-422) | >1000 (78%) | >1000 (61%) | 99 (77-129) |

TABLE 2-continued

| Cmpd | [³H] DPCPX binding to hA₁ | [³H] ZM 241385 binding to hA$_{2A}$ receptors expressed in CHO cells K$_i$(nM) | cAMP assay in CHO hA2$_{2B}$ IC$_{50}$ (nM) | [³H] MRE3008F20 binding to hA₃ receptors expressed in CHO cells K$_i$ (nM) |
|---|---|---|---|---|
| 9 | 476 (432-525) | >1000 (86%) | >1000 (99%) | 144 (136-151) |
| 10 | 2530 (2267-2824) | >5000 (96%) | 2056 (1643-2573) | 0.80 (0.60-0.90) |
| 17 | 3026 (2601-3522) | >5000 (99%) | 400 (323-496) | 8.0 (7.1-9.1) |
| 18 | >1000 (70%) | >1000 (98%) | >1000 (71%) | 3.45 (2.71-4.36) |
| 19 | >1000 (65%) | >1000 (91%) | >1000 (60%) | 80 (63-100) |
| 20 | >1000 (65%) | >1000 (99%) | >1000 (97%) | 15 (9-27) |
| 21 | 460 (424-498) | >1000 (91%) | >1000 (77%) | 31 (25-38) |
| 22 | >1000 (51%) | >1000 (99%) | >1000 (86%) | 99 (77-129) |
| 23 | 350 (299-411) | >1000 (98%) | >1000 (79%) | 23 (18-29) |
| 24 | >1000 (72%) | >1000 (99%) | >1000 (71%) | 555 (467-660) |
| 25 | >1000 (84%) | >1000 (92%) | >1000 (82%) | 36 (31-43) |
| 26 | >1000 (80%) | >1000 (97%) | >1000 (73%) | 60 (53-69) |
| 27 | >1000 (96%) | >1000 (99%) | >1000 (88%) | >1000 (93%) |

Among the 7-aryl-substituted series it was observed that substitution at the 4-position of the phenyl ring with a methoxy function or especially with the small electron-withdrawing fluorine atom, which is also able to form hydrogen bonds, produces an increase in affinity, while the introduction of a p-phenyl group leads to the total loss of affinity. This suggests that the presence of a large aromatic and lipophilic moiety, such as the biphenyl, at the 7-position of the corresponding tricyclic derivative establishes repulsive interactions with the receptor.

A series of 1,3-dipropyl-, 1,3-diisobutyl- and 1,3-dimethyl-analogs were prepared to evaluate Priego's hypothesis regarding the primary role of 1-benzyl-3-propyl-substitution on the affinity of the A₃ receptor for these compounds. Replacement of the 1-benzyl moiety in Compound 2 with a propyl or isobutyl chain, Compounds 8 and 9, respectively, led to a substantial maintenance of A₃ receptor affinity, while inducing at the same time a significant loss of selectivity versus the adenosine hA₁ subtype.

The contents of all references, patents and patent applications are hereby incorporated herein by reference. Other embodiments are within the following claims.

What is claimed is:

1. A compound of Formula (I):

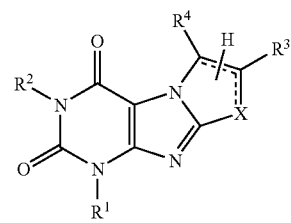

(I)

wherein

X is CH or N;

R¹ and R² are each independently alkyl, substituted alkyl, aralkyl, substituted aralkyl, alkenyl, substituted alkenyl, alkynyl, substituted alkynyl, aryl, or substituted aryl, providing R¹ and R² are not both methyl;

R³ is aryl, substituted aryl, alkyl, substituted alkyl, aralkyl, or substituted aralkyl, providing R³ is not aryl or substituted aryl when X is CH and R¹ and R² are both n-propyl;

R⁴ is hydrogen, alkyl, substituted alkyl, aralkyl, substituted aralkyl, aryl, or substituted aryl; and one of the dashed lines represents a double bond and the other represents a single bond;

or a pharmaceutically acceptable salt thereof.

2. A compound according to claim 1 having Formula (Ia):

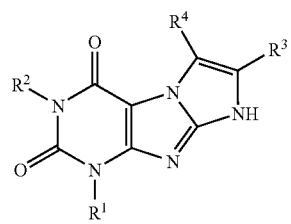

(Ia)

wherein R¹, R², R³ and R⁴ are as defined in claim 1.

3. A compound according to claim 2, wherein R⁴ is hydrogen, alkyl, or substituted alkyl.

4. A compound according to claim 2, wherein R³ is alkyl, substituted alkyl, aryl, substituted aryl, or aralkyl.

5. A compound according to claim 2, wherein R¹ and R² are each independently alkyl, substituted alkyl, or aralkyl.

6. A compound according to claim 1 having Formula (Ib):

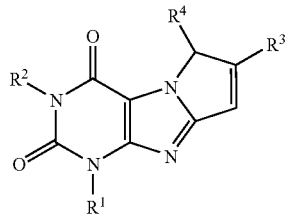

(Ib)

wherein $R^1$, $R^2$, $R^3$ and $R^4$ are as defined in claim 1.

7. A compound according to claim 6, wherein $R^4$ is hydrogen, alkyl, or substituted alkyl.

8. A compound according to claim 6, wherein $R^3$ is alkyl, substituted alkyl, aryl, substituted aryl, or aralkyl, providing $R^3$ is not aryl or substituted aryl when $R^1$ and $R^2$ are both n-propyl.

9. A compound according to claim 6, wherein $R^1$ and $R^2$ are each independently alkyl, substituted alkyl, or aralkyl, providing $R^1$ and $R^2$ are not both methyl.

10. A compound according to claim 1 which is selected from the group consisting of:
1-Benzyl-7-phenyl-3-propyl-1H-pyrrolo[1,2-f]purine-2,4(3H,6H)-dione;
1-Benzyl-7-phenyl-3-propyl-1H-imidazo[1,2-f]purine-2,4(3H,8H)-dione;
1-Benzyl-7-(4-methoxyphenyl)-3-propyl-1H-imidazo[1,2-f]purine-2,4(3H,8H)-dione;
1-Benzyl-7-(biphenyl-4-yl)-3-propyl-1H-imidazo[1,2-f]purine-2,4(3H,8H)-dione;
1-Benzyl-7-(4-fluorophenyl)-3-propyl-1H-imidazo[1,2-f]purine-2,4(3H,8H)-dione;
7-Phenyl-1,3-dipropyl-1H-imidazo[1,2-f]purine-2,4(3H,8H)-dione;
1,3-Diisobutyl-7-phenyl-1H-imidazo[1,2-f]purine-2,4(3H,8H)-dione;
1-Benzyl-7-methyl-3-propyl-1H-imidazo[1,2-f]purine-2,4(3H,8H)-dione;
1-Benzyl-7-methyl-3-propyl-1H-pyrrolo[1,2-f]purine-2,4(3H,6H)-dione;
1-Benzyl-7-ethyl-3-propyl-1H-pyrrolo[1,2-f]purine-2,4(3H,6H)-dione;
1-Benzyl-6,7-dimethyl-3-propyl-1H-pyrrolo[1,2-f]purine-2,4(3H,6H)-dione;
1-Benzyl-7-ethyl-3-propyl-1H-imidazo[1,2-f]purine-2,4(3H,8H)-dione;
1-Benzyl-7-isopropyl-3-propyl-1H-imidazo[1,2-f]purine-2,4(3H,8H)-dione;
1-Benzyl-7-tert-butyl-3-propyl-1H-imidazo[1,2-f]purine-2,4(3H,8H)-dione;
1-Benzyl-7-cyclopropyl-3-propyl-1H-imidazo[1,2-f]purine-2,4(3H,8H)-dione;
1-Benzyl-7-cyclohexyl-3-propyl-1H-imidazo[1,2-f]purine-2,4(3H,8H)-dione;
1-Benzyl-6,7-dimethyl-3-propyl-1H-imidazo[1,2-f]purine-2,4(3H,8H)-dione; and
1-Benzyl-7-ethyl-6-methyl-3-propyl-1H-imidazo[1,2-f]purine-2,4(3H,8H)-dione;
or a pharmaceutically acceptable salt thereof.

11. A compound according to claim 1 which is 1-benzyl-7-methyl-3-propyl-1H-imidazo[1,2-f]purine-2,4(3H,8H)-dione; or a pharmaceutically acceptable salt thereof.

12. A method of treating a medical condition is selected from the group consisting of cerebral ischemia, inflammation, and asthma, which method comprises administering to a mammal a therapeutically effective amount of a compound of claim 1.

13. A pharmaceutical composition comprising a compound of claim 1 and a pharmaceutically acceptable carrier.

14. A pharmaceutical composition according to claim 13 for the treatment of cerebral ischemia, inflammation and asthma.

15. A compound having the formula

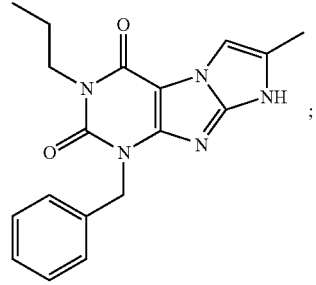

or a pharmaceutically acceptable salt thereof.

16. A method of treating a medical condition selected from the group consisting of cerebral ischemia, inflammation and asthma, which method comprises administering to a mammal a therepeutically effective amount of a compound of claim 15.

17. A pharmaceutical composition comprising a compound of claim 15 and a pharmaceutically acceptable carrier.

18. A pharmaceutical composition according to claim 17 for the treatment of cerebral ischemia, inflammation and asthma.

* * * * *